United States Patent [19]

Schelling et al.

[11] 3,968,235

[45] July 6, 1976

[54] COMPOSITION AND METHOD FOR COMBATING INSECTS WITH ALKYLENEDIOXYPHENYL DERIVATIVES

[75] Inventors: Hans-Peter Schelling, Oberwil; Fritz Schaub, Basel, both of Switzerland

[73] Assignee: Sandoz Ltd., Basel, Switzerland

[22] Filed: May 23, 1974

[21] Appl. No.: 472,918

Related U.S. Application Data

[63] Continuation-in-part of Ser. No. 207,633, Dec. 13, 1971, Pat. No. 3,829,442.

[30] Foreign Application Priority Data

Dec. 14, 1970 Switzerland.................. 18472/70
Sept. 17, 1971 Switzerland.................. 13599/71
Oct. 6, 1971 Switzerland.................. 14521/71
Nov. 11, 1971 Switzerland.................. 16357/71

[52] U.S. Cl. ................................ 424/282
[51] Int. Cl.² ............................... A01N 9/28
[58] Field of Search ........................ 424/282

[56] References Cited
UNITED STATES PATENTS

| 3,709,914 | 1/1973 | Siddall | 260/340.5 |
| 3,709,915 | 1/1973 | Siddall | 260/340.5 |
| 3,787,443 | 1/1974 | Erickson | 260/327 E |

FOREIGN PATENTS OR APPLICATIONS

| 2,103,733 | 4/1972 | France |
| 1,144,906 | 3/1969 | United Kingdom |

OTHER PUBLICATIONS

Ellis et al., "Pans" vol. 16 (No. 3) 1970 – pp. 434–446.
Chang et al.: "Agr. Biol. Chem." 35 (8) pp. 1307–1309.
Borkovec, "Insect Chemosterilants" — Interscience Publ. — John Wiley & Sons — New York pp. 61–63 (1966).
Ann. Rev. of Bioch. — Slama—Am. Rev. Inc. — Palo Alto, Cal. — pp. 1079, 1096 & 1097 (1971).

*Primary Examiner*—Albert T. Meyers
*Assistant Examiner*—D. W. Robinson
*Attorney, Agent, or Firm*—Gerald D. Sharkin; Richard E. Vila

[57] ABSTRACT

The present invention concerns the use of the compounds of the formula:

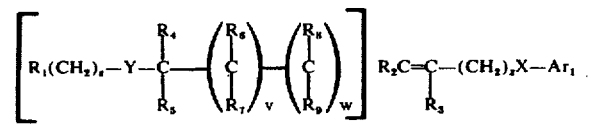

wherein $R_1$ to $R_9$ have various significances including e.g. alkyl, X and Y include O and S, and $s$, $v$, $w$ and $z$ are O or whole numbers and $Ar_1$ is substituted phenyl, as insecticides, and insecticidal compositions containing said compounds as active agent.

12 Claims, No Drawings

COMPOSITION AND METHOD FOR COMBATING INSECTS WITH ALKYLENEDIOXYPHENYL DERIVATIVES

This application is a continuation-in-part of our co-pending application Ser. No. 207,633, filed Dec. 13, 1971, now U.S. Pat. No. 3,829,442.

The present invention relates to ethers and thioethers and more specifically to aromatic ethers and thioethers.

The present invention provides compounds of formula I,

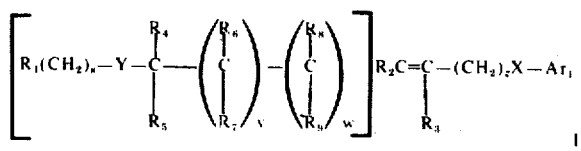

wherein $Ar_1$ is

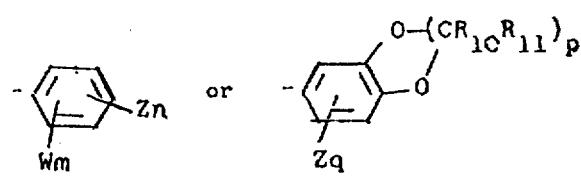

Wherein
W is alkyl of 1 to 5 carbon atoms, fluorine, chlorine or bromine,
Z is alkyl of 1 to 5 carbon atoms, alkenyl of 2 to 12 carbon atoms, alkoxy of 1 to 5 carbon atoms, alkenyloxy of 2 to 12 carbon atoms, formyl, alkyl carbonyl of 2 to 6 carbon atoms, alkoxy carbonyl of 2 to 6 carbon atoms, mono- or di- alkyl substituted carbamoyl each alkyl substituent being of 1 to 5 carbon atoms, alkoxy methylene of 2 to 6 carbon atoms, alkylthio of 1 to 5 carbon atoms, fluorine, chlorine, bromine, cyano or nitro,
$R_{10}$ and $R_{11}$, which may be the same or different, are each hydrogen or alkyl of 1 to 5 carbon atoms,
$n$ and $p$, which may be the same or different, are each 1 or 2,
$q$ is 0 or 1,
$m$ is 0, 1, 2, 3 or 4,
$R_1$ is alkyl of 1 to 11 carbon atoms, non-cyclic hydrocarbon of up to 11 carbon atoms having one or two double bonds or one triple bond, cycloalkyl of 4 to 7 carbon atoms, alkyl substituted cycloalkyl of 4 to 7 ring carbon atoms the alkyl substituent having 1 to 5 carbon atoms, cycloalkenyl of 4 to 7 carbon atoms, alkyl substituted cycloalkenyl of 4 to 7 ring carbon atoms the alkyl substituent having 1 to 5 carbon atoms, phenyl, $Ar_2$ which has the same definition as $Ar_1$ above wherein $Ar_1$ and $Ar_2$ may be the same or different,
$R_2$, $R_3$, $R_4$, $R_5$, $R_6$, $R_7$, $R_8$ and $R_9$, which may be the same or different, are each hydrogen, alkyl of 1 to 5 carbon atoms or alkenyl of 2 to 6 carbon atoms,
Y is oxygen or sulphur
X is oxygen, sulphur, $-OCH_2-$ or $-SCH_2-$,
$s$, $v$ and $w$, which may be the same or different, are each 0, or 1 and
$z$ is 1, 2 or 3.

It is to be understood that the terms alkyl, alkenyl, alkoxy and non-cyclic hydrocarbon cover both straight and branched chain configurations thereof.

The present invention also provides a process for the production of a compound of formula I, which comprises a. reacting a compound of formula II,

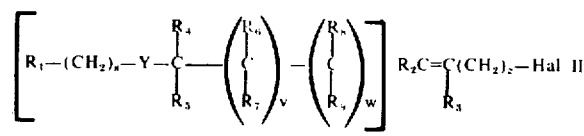

wherein
$R_1$, $R_2$, $R_3$, $R_4$, $R_5$, $R_6$, $R_7$, $R_8$, $R_9$, Y, $s$, $v$, $w$ and $z$ are as defined above and
· Hal is chlorine or bromine,
with a compound of formula III, $$MX-Ar_1 \qquad III$$

wherein
$Ar_1$ and X are as defined above and
M is hydrogen, potassium or sodium,
with the proviso that when M is hydrogen, the reaction is effected in the presence of an acid binding agent, b. reacting a compound of formula IV,

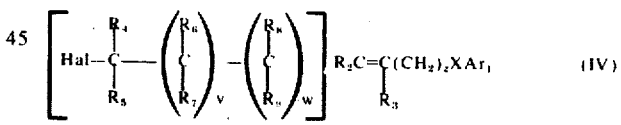

wherein
$R_2$, $R_3$, $R_4$, $R_5$, $R_6$, $R_7$, $R_8$, $R_9$, X, $Ar_1$, $v$ and $w$ are as defined in relation to formula I,
Hal is chlorine or bromine and
$z$ is 1,
with the proviso that $v + w$ is 0 or 2 or when $v + w$ is 1, $R_6$ and $R_7$, or $R_8$ and $R_9$ are other than hydrogen,
with an alcoholate or thioalcoholate of formula V, $$R_1(CH_2)_sYMe \qquad V$$

wherein
$R_1$, Y and $s$ are as defined in relation to formula I, and
Me is sodium or potassium,
to produce a compound of formula Ia i.e. a compound of formula I wherein $z$ is 1, $v + w$ is 0 or 2, or when $v + w$ is 1, $R_6$ and $R_7$, or $R_8$ and $R_9$ are other than hydrogen c. condensing a compound of formula VIa,

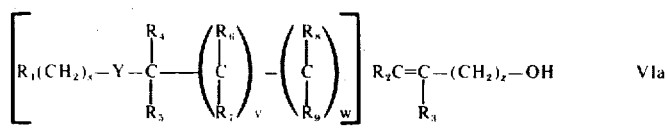

wherein $R_1$, $R_2$, $R_3$, $R_4$, $R_5$, $R_6$, $R_7$, $R_8$, $R_9$, Y, s, v, w and z are as defined in relation to formula I,
with a compound of formula IIIa $$Ar_1OH \qquad \text{IIIa}$$

wherein $Ar_1$ is as defined in relation to formula I, in the presence of dicyclohexylcarbodiimide as condensation agent, to produce a compound of Ib, i.e. a compound of formula I wherein X is oxygen,
or
d. reacting a compound of formula VIa or VIb,

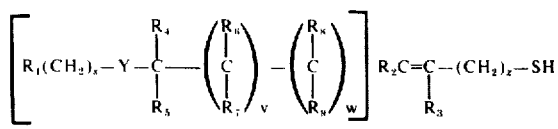

wherein $R_1$, $R_2$, $R_3$, $R_4$, $R_5$, $R_6$, $R_7$, $R_8$, $R_9$, Y, s, v, w and z are as defined in relation to formula I,
or an alkali alcoholate or thioalcoholate thereof respectively with a compound of formula VII, $$Hal-CH_2-Ar_1 \qquad \text{VII}$$

wherein
$Ar_1$ is as defined in relation to formula I and
Hal is chlorine or bromine,
with the proviso that when a compound of formula VIa or VIb is reacted in the free alcohol or thioalcohol form thereof respectively, the reaction is effected in the presence of an acid-binding agent, to produce a compound of formula Ic i.e. a compound of formula I wherein X is $-OCH_2-$ or $-SCH_2-$.

The production of compounds of formula I in accordance with process (a) may be effected as follows viz.

A compound of formula III is conveniently reacted in a solvent, for example, a hydrocarbon such as benzene, an ether such as dioxane, 1,2-dimethoxyethane, diethyleneglycol-dimethyl ether, an alcohol such as ethanol, tert.butanol, a ketone such as acetone, a nitrile such as acetonitrile, an acid amide such as dimethylformamide, or in an appropriate solvent mixture, in the presence of an acid binding agent, for example, sodium hydroxide, potassium hydroxide, sodium carbonate, potassium carbonate, potassium-tert.butoxide, at a temperature between preferably 0° and about 100°C with a compound of formula II. Potassium iodide may, conveniently be added in catalytic amounts to the reaction mixture as catalyst.

When z of formula I is 2, reaction conditions which may cause a β-elimination, e.g. the use of sodium or potassium hydroxide, in e.g. dimethylformamide as solvent, are avoided.

Working up of the reaction product is effected in the usual manner.

The production of compounds of formula Ia in accordance with process (b) may be effected as follows viz.

A compound of formula IV is reacted, conveniently in an appropriate reaction medium, for example an ether such as dioxane, 1,2-dimethoxyethane, diethyleneglycol-dimethyl ether, a hydrocarbon such as benzene, or provided that Y in formula V signifies oxygen, in an alcohol of formula $R_1(CH_2)_sOH$ wherein $R_1$ and s correspond to those of formula V, or provided that Y in formula V signifies sulphur, in a mercaptan of formula $R_1(CH_2)_sSH$ wherein $R_1$ and s correspond to those of formula V, preferably at a temperature between room temperature and about 100°C, over a period, e.g. 3 to 15 hours, with a compound of formula V. Working up of the reaction product is effected in the usual manner.

The production of compounds of formula Ib in accordance with process (c) may be effected as follows viz.

A compound of formula VIa or VIb is reacted, conveniently in an appropriate solvent, for example a hydrocarbon such as benzene, an ether such as 1,2-dimethoxyethane, an alcohol such as ethanol or tert.butanol, a ketone such as acetone, a nitrile such as acetonitrile, an acid amide such as dimethyl formamide, or in an appropriate solvent mixture, in the presence of an acid binding agent, for example sodium hydroxide and potassium hydroxide, at a temperature between 20° and 100°C with a compound of formula VII. Working up of the reaction product is effect in conventional manner.

When the compounds of formula VIa and VIb are reacted in the form of an alkali alcoholate or thioalcoholate, the reaction may be effected in the absence of an acid binding agent. The reaction may be effected in an appropriate solvent, such as benzene, tert.butanol, 1,2-dimethoxyethane, dimethylformamide. Working up is effected in the usual manner.

The compounds of formula I are generally colourless oils or crystalline and may be characterized in the usual manner.

The compounds of formula II employed as starting material in the production of compounds of formula I in accordance with process (a) above, may be produced by a process as follows viz.

a'. Reacting a compound of formula VIII,

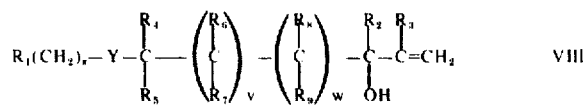

wherein $R_1$, $R_2$, $R_3$, $R_4$, $R_5$, $R_6$, $R_7$, $R_8$, $R_9$, Y, s, v, and w are as defined in relation to formula I,
with a halide transmitter e.g. hydrobromic acid, thionyl halides or a suitable phosphorous halide in the presence of an acid binding agent to obtain a compound of formula IIa i.e. a compound of formula II, wherein z is 1.

b'. Reacting a compound of formula XI,

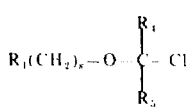 XI wherein $R_1$, $R_4$, $R_5$ and $s$ are as defined in relation to formula I,
with a compound of formula XII,

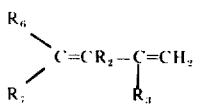 XII wherein $R_2$, $R_3$, $R_6$ and $R_7$ are as defined in relation to formula I,
if required, in the presence of an appropriate catalyst, such as anhydrous zinc chloride, to produce a compound of formula IIb i.e. a compound of formula II wherein Y is oxygen, Hal is chlorine, $z$ and $v$ are 1 and $w$ is 0.

c'. Reacting a compound of formula VIa, wherein $z$ is 3, with an appropriate halide transmitter e.g. hydrobromic acid, a thionylhalide or a suitable phosphorous halide in the presence of an acid binding agent, to produce a compound of formula IIc i.e. a compound of formula II, wherein $z$ is 3.

d'. Reacting a compound of formula XIIIa,

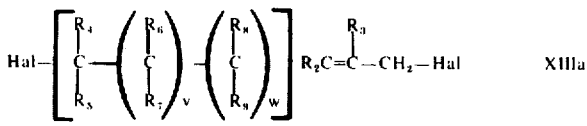 XIIIa wherein
$R_2$, $R_3$ are as defined in relation to formula I,
Hal is chlorine or bromine,
each of $R_4$, $R_5$, $R_6$, $R_7$, $R_8$ and $R_9$ is hydrogen,
and each of $v$ and $w$ is 0 or 1,
with a compound of formula V, to produce a compound of formula IId i.e. a compound of formula II, wherein $R_1$ and $R_5$ is hydrogen, and each of $v$ and $w$ is 0.

e'. Reacting a compound of formula XIV,

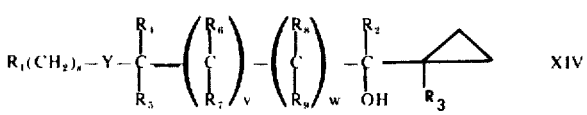 XIV wherein $R_1$, $R_2$, $R_3$, $R_4$, $R_5$, $R_6$, $R_7$, $R_8$, $R_9$, Y, $s$, $v$ and $w$ are as defined in relation to formula I,
with concentrated hydrochloric or hydrobromic acid, preferably of 48% by weight concentration, to produce a compound of formula IIe i.e. a compound of formula II, wherein $z$ is 2 and Hal is chlorine or bromine.

The production of compounds of formula IIa in accordance with process (a') may be effected as follows viz.

The reaction temperature and solvent depend on the halide transmitter employed. Thus, with 48% by weight hydrogen bromide or hydrochloric acid no solvent is required and the reaction temperature may be between −20° and 0°C. With thionylhalides, a suitable solvent is ether and a suitable reaction temperature is room temperature. With phosphorous halides, e.g. phosphorous tribromide, pyridine may be employed as solvent which also serves as acid binding agent and a suitable reaction temperature is between −20° and 0°C.

The purification of the resulting compound of formula IIa may, if desired be omitted, and the compound may be employed directly in the production of compounds of formula I in accordance with process (a) above.

The compounds of formula VIII employed as starting material in process (a') above may, for example, be produced by reacting a compound of formula IX,

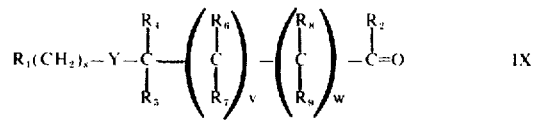 IX wherein $R_1$, $R_2$, $R_4$, $R_5$, $R_6$, $R_7$, $R_8$, $R_9$, Y, $s$, $v$, and $w$ are as defined in relation to formula I,
with a compound of formula X,

 X wherein
$R_3$ is as defined above and
Mt is —MgCl, —MgBr or Li in organometalic bond, in an appropriate solvent, such as tetrahydrofuran, and subsequent hydrolysis of the resulting magnesium or lithium compound in the usual manner.

The compounds of formulae IX and X employed in the production of compounds of formula VIII above are known or may be produced in accordance with known methods.

The production of compounds of formula IIb in accordance with process (b') may be effected as follows viz.

The reaction may be effected with or without a solvent. An example of a suitable solvent is ether. The reaction temperature may vary between 0° and 30°C.

The starting compounds of formula XI and XII employed in process (b') above are either known or may be produced in accordance with known methods.

The production of compounds of formula IIc in accordance with process (c') above may be effected as follows viz.

The reaction conditions will vary with the actual halide transmitter employed. Thus, with 48% by weight hydrogen bromide no solvent is required and a suitable reaction temperature is between −20° and 0°C. With thionylhalides a suitable solvent is ether or benzene and a suitable reaction temperature is between −10° and 25°C. With phosphorous halides e.g. phosphorous tribromide, a suitable solvent and acid binding agent is pyridine the reaction temperature varying between −20°C and room temperature.

The starting compounds of formula VIa, wherein $z$ is 3 employed in process (c') and also in process (c) above for the production of some of the compound of formula Ib and in process (d) above for the production of some of the compounds of formula Ic, may be produced by sodium bromohydride reduction of a compound of formula XVI,

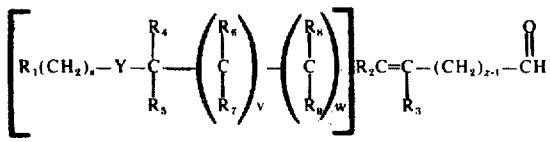

wherein
$R_1$, $R_2$, $R_3$, $R_4$, $R_5$, $R_6$, $R_7$, $R_8$, $R_9$, Y, s, v and w are as defined in relation to formula I, and
z is 3,
in manner known per se.

The compounds of formula XVI, may, for example, be obtained by reacting the compounds of formula VIII with alkyl vinyl ethers in the presence of mercury-II-acetate at an elevated temperature, preferably for a period of e.g. 4 days, and subsequent transposition by short heating to 160°–190°C, preferably over 1 to 2 hours.

The production of compounds of formula IId in accordance with process (d') may be effected as follows viz. The compounds of formulae V and XIIIa are dissolved in a suitable solvent e.g. an alcohol of formula $R_1(CH_2)_sCH$ or thioalcohol of formula $R_1(CH_2)_sSH$ wherein $R_1$ and s correspond to those of formula V, an acid amide e.g. dimethyl formamide, or a sulphoxide e.g. dimethyl sulphoxide and the reaction is effected at a temperature of between 0° and 100°C preferably between 20° and 30°C.

The starting compounds of formula XIIIa employed in process (d') above are either known or may be produced in accordance with known methods.

The production of compounds of formula IIe in accordance with process (e') may be effected as follows:

The compound of formula XIV and either 48% by weight hydrogen bromide or concentrated hydrochloric acid are reacted at a temperature of about 0°C. A solvent is not required.

The compounds of formula XIV employed as starting material in process (e') above may be produced by reacting a compound of formula IX with a Grignard compound of formula XV,

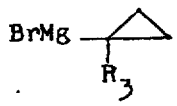

wherein $R_3$ is as defined in relation to formula I, and subsequent hydrolysis of the magnesium compound.

The compounds of formula III employed as a starting material in process (a) above for the production of compounds of formula I, are known.

The compounds of formula IV, employed as a starting material in process (b) above for the production of compounds of formula Ia may be produced by reacting a compound of formula XIII,

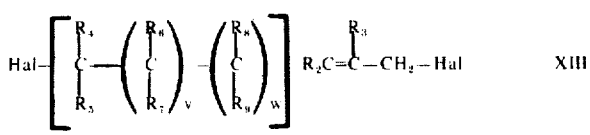

wherein
$R_2$, $R_3$, $R_4$, $R_5$, $R_6$, $R_7$, $R_8$, $R_9$, v and w are as defined in relation to formula I and Hal is chlorine or bromine,
with a compound of formula III, with the proviso that when M of formula III is hydrogen, the reaction is effected in the presence of an acid binding agent.

The compounds of formula V employed as a starting material in process (b) above for the production of compounds of formula Ia are known or may be produced in accordance with known methods.

The compounds of formula VIa employed as a starting material in process (b) and (d) above for the production of compounds Ib and Ic respectively, when z is 3 has already been described. The production of compounds of formula VIa when z is 1 or 3 may be effected by reacting a compound of formula II, wherein z is 1 or 3, with aqueous alkali e.g. potassium hydroxide in manner known per se.

The compounds of formula VIa when z is 2 may be effected by reacting a compound of formula II wherein z is 2 with potassium acetate, preferably in glacial acetic acid under reflux and hydrolysing the resulting acetate with methanolic potassium hydroxide.

The compound of formula VIb employed as a starting material in process (d) above for the production of some of the compounds of formula Ic, wherein z is 1 or 3 may be produced as follows viz.

Reacting a compound of formula II, wherein z is 1 or 3 with thiourea or ammonium dithiocarbamate in water at about 100°C and subsequent alkaline hydrolysis of the resulting compound with e.g. 5N potassium hydroxide.

The compounds of formula VIb, wherein z is 2 may, for example, be produced by reacting a compound of formula II, wherein z is 2 with an alkali thioacetate e.g. potassium thioacetate, in e.g. dimethyl sulphoxide or acetonitrile, as solvent followed by alkaline hydrolysis e.g. with methanolic potassium hydroxide.

The compounds of formula I are useful as insecticides as indicated by exhibiting an inhibiting effect on the development of the insects:

*Dysdercus Fasciatus* (Egyptian cotton worm)
*Prodenia - littura* (cotton stainer)
*Tenebrio - molitor* (flour beetle) and
*Tetranychus urticae* (red spider)

from one development stage thereof to the next, to result either in death or reduced oviposition or inhibition of copulation as indicated by the following tests viz.

TEST 1

Insecticidal effect on *Dysdercus fasciatus* larvae
(Egyptian cotton worm)

Filter paper is impregnated with a solution of a compound of formula I. A box made from polystyrene (200 × 100 × 85 mm) is coated with the filter paper treated in this way. A folded filter paper which is also impregnated and covered with about 30 Dysdercus larvae of the fourth larval stage is placed into this box. Pounded cotton seeds as food and a drinking-vessel are placed into it. The number of adults which have developed normally after 14 to 15 days is determined.

TEST 2

Effect on the development of *Prodenia-littura* larvae (cotton stainer) into adults Filter paper is impregnated with a solution of a compound of formula I. Partitions, having a size of 3.5 × 5.5 cm, of a plastic box are coated with the filter paper treated in this way. One Prodenia caterpiller in the third to fourth larval stage is placed into each partition and a piece of artificial medium is given as food. The insects are kept at 25°. The number of the adults which have developed normally after 21 days is determined.

TEST 3

Effect on the development of *Tenebrio-molitor* chrysales (flour beetle) into adults A compound of formula I is used at a concentration of 1% by weight in acetonic solution. 2 μl of the resulting solution, corresponding to 20 micrograms of compound, are applied on the abdominal side of the last three segments of young chrysales (not older than 18 hours) by means of a 1-microliter bulb pipette. 10 chrysales are used for each test. The treated chrysales are kept at 28° in plastic cups. The adults which have developed normally are counted after 10 to 12 days.

TEST 4

Contact effect in *Tetranychus urticae* (red spider)

One day before treatment 10 adult females of *Tetranychus urticae* are placed by means of a pencil between two rings (diameter : 3 cm) of caterpiller lime which are applied to a leaf of a cotton plant. The cotton leaves are sprayed to run off by means of a sprayer with a liquor containing 0.1% by weight of a compound of formula I. After drying, the plants are kept at room temperature and in light. The dead and live insects are counted 6 days after the treatment. The relation between the treated and one untreated population shows the effect.

From $LD_{50}$ oral or dermal determinations on the male rat, a low toxicity of the compounds of formula I towards warm blooded animals is indicated.

For the abovementioned use, the amount applied to a locus to be treated e.g. a plant culture, will of course vary depending on the compound employed, the mode of application, ambient conditions, and the insects to be combated. However, in general satisfactory results are obtained when a compound of formula I is applied to the locus in an amount between 1 and 10 kg/hectare, the application being repeated as required.

The compounds may be applied to the locus with conventional applicator equipment and by conventional methods e.g. strewing, spraying and dusting.

Compositions may be produced in conventional manner and may comprise a compound of formula I in admixture with insecticidal carriers e.g. talc, diatomaceous earth, bentonite and pumice, insecticidal diluents e.g. water or appropriate organic solvents such as alcohols, petroleum and tar distillates and/or insecticidal adjuvants e.g. emulsifying agents, solvent aids such as mineral oils and wetting and adhesive agents such as cellulose derivatives.

Concentrate forms of the compositions may generally contain between 2 and 90%, preferably between 5 and 50% by weight, of a compound of formula I.

Application forms of the composition may generally contain between 0.01 and 0.1%, by weight of a compound of formula I.

Preferred compounds of formula I are as follows:

5-(5-tert.butoxy-3-methyl-2-pentenyloxy)-1,3-benzodioxol, 5-(5-isopropylthio-3-methyl-2-pentenyloxy)-1,3-benzodioxol, 4-(3-ethyl-5-sec.butoxy-2-pentenyloxy)-benzoic methyl ester, 4'-(3-ethyl-5-sec. butoxy-2-pentenyloxy)-acetophenone, 5-(5-cyclopentyloxy-3-methyl-2-pentenyloxy)-1,3-benzodioxol, 5-[3-methyl-5-(2-pentyloxy)-2-pentenyloxy]-1,3-benzodioxol, 5-[(5-isopropoxy-3-methyl-2-pentenyloxy)-methyl]-1,3-benzodioxol, 5-(5-isopropoxy-3-methyl-2-pentenyloxy)-1,3-benzodioxol, 4-(5-isopropoxy-3-methyl-2-pentenylthio)-chlorobenzene, 4-(5-isopropoxy-3-methyl-2-pentenyloxy)-thioanisole, 4-(5-isopropoxy-3-methyl-2-pentenyloxy)-ethylbenzene, 5-(5-ethoxy-3-methyl-2-pentenyloxy)-1,3-benzodioxoal, 4-(6-ethoxy-3-methyl-2-hexenyloxy)-benzoic acid methyl ester, 4'-(6-ethoxy-3-methyl-2-hexenyloxy)-acetophenone, 5-(4-isobutoxy-2-methyl-2-butenyloxy)-1,3-benzodioxol, 5-(6-isopropoxy-4-methyl-3-hexenyloxy)-1,3-benzodioxol, The following Examples illustrate the production of the compounds of formula I; but in no way limit the invention. The temperatures are indicated in degrees Centigrade. Where concentration is indicated as a %, this is % by weight.

EXAMPLE 1

2-(3-Ethyl-5-sec. butoxy-2-pentenyloxy)-benzaldehyde (according to process a)

9.3 g (0.05 mol) of 3-ethyl-5-sec.butoxy-1-penten-3-ol are added dropwise at 5° in the course of 15 minutes and while stirring to 20 cc of 48% hydrobromic acid. After stirring the mixture vigorously at 5° to 10° for half an hour it is extracted with ether, the ether extract is extracted with 10% soda solution and subsequently with saturated solution of sodium chloride, is dried with potassium carbonate and concentrated by evaporation. The resulting 1-bromo-3-ethyl-5-sec.butoxy-2-pentene is added without purification to 6.1 g (0.05 mol) of salicylic aldehyde and 2.8 g (0.05 mol) of potassium hydroxide in 80 cc of 1,2-dimethoxy ethane. The mixture is stirred at 20°-25° for 24 hours, is subsequently filtered and concentrated by evaporation at reduced pressure. The residue is taken up in ether, extracted with icy cold 10% sodium hydroxide solution and subsequently with saturated salt solution, is dried with sodium sulphate and evaporated.

The obtained 2-(3-ethyl-5-sec.butoxy-2-pentenyloxy)-benzaldehyde may be purified by chromatography on silica gel with hexane/ethyl acetate 1 : 1 as eluant. $n_D^{20}$: 1.5090.

| Analysis: | $C_{18}H_{26}O_3$ | | Molecular weight: | 290.4 |
|---|---|---|---|---|
| Calc. | C 74.4 % | | H 9.0 % | |
| Found | 74.1 % | | 9.2 % | |

In analogous manner to that described in the preceding examples and employing appropriate starting materials, the following compounds are produced viz:

2-[6-(2,5-dimethylheptyloxy)-2,3,4,4,6,6,-hexamethyl-2-hexenyloxy)-methyl]-benzaldehyde,
2-(5-allyloxy-3,4,5-trimethyl-2-pentenyloxy)-benzaldehyde,
3-chloro-4-(3-ethyl-5-sec. butoxy-2-pentenyloxy)-benzaldehyde,
2-[6-(2,5-dimethylheptyloxy)-2,3,4,4,6,6,hexamethyl-2-hexenyloxy)-methyl]-benzoic n-pentyl ester,
2-(5-allyloxy- 3,4,5-trimethyl-2-pentenyloxy)-benzoic methyl ester,
3-methyl-4-(3-ethyl-5-isopropoxy-2-pentenyloxy)-benzoic methyl ester,
3-chloro-4-(3-ethyl-5-sec.butoxy-2-pentenyloxy)-benzoic ethyl ester,
2'-[6-(2,5,-dimethylheptyloxy)-2,3,4,4,6,6,-hexamethyl-2-hexenyloxy)-methyl]-acetophenone,
3'-methyl-4'-(3-ethyl-5-isopropoxy-2-pentenyloxy)-acetophenone,
3'-chloro-4'-(3-ethyl-5-sec.butoxy-2-pentenyloxy)-acetophenone,
4-[6-(2,5-dimethylheptyloxy)-2,3,4,4,6,6,-hexamethyl-2-hexenyloxy]-methyl-dimethyl carbamoyl benzene and
1-(5-allyloxy-3-ethyl-2-pentenyloxy)-2,4,-dimethyl benzene.

| Example | | Empirical formula | Molecular weight | $n_D^{20}$ | Analysis % Calc. Found C | H | S | Starting compound of formula VIII produced in example No. |
|---|---|---|---|---|---|---|---|---|
| 2 | 2-(3-Ethyl-5-isopropoxy-2-pentenyloxy)benzaldehyde | $C_{17}H_{24}O_3$ | 276.4 | 1.5194 | 73.9 / 73.5 | 8.8 / 9.1 | | 64 |
| 3 | 4-(3-Ethyl-5-isopropoxy-2-pentenyloxy)benzaldehyde | $C_{17}H_{24}O_3$ | 276.4 | 1.5290 | 73.9 / 74.3 | 8.8 / 8.8 | | 64 |
| 4 | 5-(3-Ethyl-5-sec.butoxy-2-pentenyloxy)-1,3-benzodioxol | $C_{18}H_{26}O_4$ | 306.4 | 1.5104 | 70.6 / 70.1 | 8.6 / 8.1 | | 66 |
| 5 | 5-(3-Ethyl-5-isopropoxy-2-pentenyloxy)-1,3-benzodioxol | $C_{17}H_{24}O_4$ | 292.4 | 1.5128 | 69.8 / 69.0 | 8.3 / 8.7 | | 64 |
| 6 | 5-(5-tert.Butoxy-3-methyl-2-pentenyloxy)-1,3-benzodioxol | $C_{17}H_{24}O_4$ | 292.4 | 1.5124 | 69.8 / 69.3 | 8.3 / 8.0 | | 67 |
| 7 | 5-(5-Isopropylthio-3-methyl-2-pentenyloxy)-1,3-benzodioxol | $C_{16}H_{22}O_3S$ | 294.4 | 1.5481 | 65.4 / 65.8 | 7.5 / 7.8 | 10.9 / 11.0 | 68 |
| 8 | 5-(5-Cyclohexyloxy-3-methyl-2-pentenyloxy)-1,3-benzodioxol | $C_{19}H_{26}O_4$ | 318.4 | 1.5310 | 71.7 / 71.9 | 8.2 / 8.4 | | 70 |
| 9 | 4-(3-Ethyl-5-sec.butoxy-2-pentenyloxy)benzoic methyl ester | $C_{19}H_{28}O_4$ | 320.4 | 1.5114 | 71.2 / 71.5 | 8.8 / 8.9 | | 66 |
| 10 | 4-(3-Ethyl-5-isopropoxy-2-pentenyloxy)benzoic methyl ester | $C_{18}H_{26}O_4$ | 306.4 | 1.5153 | 70.6 / 70.7 | 8.6 / 8.9 | | 64 |
| 11 | 4-(5-tert.Butoxy-3-methyl-2-pentenyloxy)benzoic methyl ester | $C_{18}H_{26}O_4$ | 306.4 | 1.5143 | 70.6 / 70.9 | 8.6 / 8.9 | | 67 |
| 12 | 4-(5-Isopropylthio-3-methyl-2-pentenyloxy)benzoic methyl ester | $C_{17}H_{24}O_3S$ | 308.4 | 1.5461 | 66.2 / 66.1 | 7.8 / 8.1 | 10.4 / 10.5 | 68 |
| 13 | 4'-(3-Ethyl-5-sec.butoxy-2-pentenyloxy)acetophenone | $C_{19}H_{28}O_3$ | 304.4 | 1.5214 | 75.0 / 75.0 | 9.3 / 9.4 | | 66 |

| Example | | Empirical formula | Molecular weight | $n_D^{20}$ | Analysis % Calc. Found C | H | Starting compound of formula VIII produced in Example No. |
|---|---|---|---|---|---|---|---|
| 14 | 4-(5-Cyclohexyloxy-3-methyl-2-pentenyloxy)-benzoicacid-methylester | $C_{20}H_{28}O_4$ | 332.4 | 1.5299 | 72.3 / 72.7 | 8.5 / 8.8 | 70 |
| 15 | 4'-(3-ethyl-5-sec.butoxy-2-pentenyloxy)-butyrophenone | $C_{21}H_{32}O_3$ | 332.5 | 1.5154 | 75.9 / 76.4 | 9.7 / 9.8 | 66 |
| 16 | 4-(3-ethyl-5-sec.butoxy-2-pentenyloxy)-benzoicacid-isopropylester | $C_{21}H_{32}O_4$ | 348.5 | 1.5037 | 72.4 / 72.6 | 9.3 / 9.5 | 66 |
| 17 | 5-(5-Cyclopentyloxy-3-methyl-2-pentenyloxy)-1,3-benzodioxol | $C_{18}H_{24}O_4$ | 304.4 | 1.5301 | 71.0 / 71.3 | 7.9 / 8.1 | 71 |
| 18 | 5-[3-Methyl-5-(3-pentyloxy)-2-pentenyloxy]-1,3-benzodioxol | $C_{18}H_{26}O_4$ | 306.4 | 1.5118 | 70.6 / 70.9 | 8.6 / 8.6 | 73 |
| 19 | 5-[3-Methyl-5-(2-pentyloxy)-2-pentenyloxy]-1,3-benzodioxol | $C_{18}H_{26}O_4$ | 306.4 | 1.5080 | 70.6 / 70.5 | 8.6 / 8.9 | 72 |
| 20 | 5-(5-Methoxy-3-methyl-2-pentenyloxy)-1,3-benzodioxol | $C_{15}H_{20}O_4$ | 264.3 | 1.5240 | 68.2 / 68.3 | 7.6 / 7.5 | 75 |
| 21 | 5-(5-n.Butoxy-3-methyl-2-pentenyloxy)-1,3-benzodioxol | $C_{17}H_{24}O_4$ | 292.4 | 1.5142 | 69.8 / 69.1 | 8.3 / 8.3 | 74 |
| 22 | 5-[3-Methyl-5-(6-methyl-5-hepten-2-yl-oxy)-2-pentenyloxy]-1,3-benzodioxol | $C_{21}H_{30}O_4$ | 346.5 | 1.5160 | 72.8 / 73.0 | 8.7 / 9.0 | 77 |
| 23 | 4'-(5-ethoxy-3,5-dimethyl-2-hexenyloxy)-acetophenone | $C_{18}H_{26}O_3$ | 290.4 | 1.5263 | 74.4 / 74.4 | 9.0 / 8.9 | 76 |

EXAMPLE 24

5-(5-Isopropoxy-3-methyl-2-pentenyloxy)-1,3-benzodioxol (according to process a)

1.7 g (0.03 mol) of pulverised potassium hydroxide are added to a solution of 4.1 g (0.03 mol) of 3,4-methylendioxy-phenol and 6.2 g (0.035 mol) of 1-chloro-5-isopropoxy-3-methyl-2-pentene in 100 cc of 1,2-dimethoxyethane. The mixture is stirred at 60° for a period of 18 hours, is subsequently filtered and evaporated at reduced pressure. The residue is dissolved in ether, washed with 5% solution of sodium hydroxide and subsequently with saturated salt solution, dried with sodium sulphate and evaporated.

The remaining 5-(5-isopropoxy-3-methyl-2-pentenyloxy)-1,3-benzodioxol is purified by chromatography on silica gel with hexane/ethyl acetate 9:1. A chromatographically uniform and colourless oil is obtained which according to gas-chromatogramme and NMR-spectrum consists of a mixture of 30% of the 2-cis and 70% of the 2-trans compound. $n_D^{20}$=1.5167.

| Analysis: | $C_{16}H_{22}O_4$ | Molecular weight: | 278.3 |
|---|---|---|---|
| Calc. | C 69.0 % | H 7.9 % | |
| Found | 68.5 % | 7.9 % | |

In analogous manner as described in Example 24, but using the starting compounds of formula III indicated in the following Table, the following compounds of general formula I are obtained:

In analogous manner as described in Example 33, but using 4-hydroxy-benzoic acid-methyl ester in the place of 3,4-methylendioxyphenol, the following compound of general formula I is produced:

EXAMPLE 34

4-(6-Ethoxy-3-methyl-2-hexenyloxy)-benzoic methyl ester $n_D^{20} = 1.5202$

| Analysis: | $C_{17}H_{24}O_4$ | Molecular weight: | 292.4 |
|---|---|---|---|
| Calc. | C 69.8 % | H 8.3 % | |
| Found | 69.5 % | 82.2 % | |

In analogous manner as described in Example 33, but using p-hydroxy-acetophenone in the place of 3,4-methylendioxy-phenol, the following compound of general formula I is produced:

EXAMPLE 35

4'-(6-Ethoxy-3-methyl-2-hexenyloxy)-acetophenone

| Example | | Empirical formula | Molecular weight | $n_D^{20}$ | Analysis % Calc. Found | | | | | | Starting compound of formula III |
|---|---|---|---|---|---|---|---|---|---|---|---|
| | | | | | C | H | Br | Cl | N | S | |
| 25 | 2-(5-Isopropoxy-3-methyl-2-pentenylthio)-benzoicacid-methylester | $C_{17}H_{24}O_3S$ | 308.4 | 1.5492 | 66.2 66.9 | 7.8 7.9 | — — | — — | — — | 10.4 10.4 | 2-Mercapto-benzoicacid-methylester |
| 26 | 3-(5-Isopropoxy-3-methyl-2-pentenyloxy)-bromobenzol | $C_{15}H_{21}BrO_2$ | 313.2 | 1.5138 | 57.5 58.1 | 6.8 7.0 | 25.5 25.1 | — — | — — | — — | 3-Bromo-phenol |
| 27 | 4-(5-Isopropoxy-3-methyl-2-pentenylthio)-chlorobenzol | $C_{15}H_{21}ClOS$ | 284.8 | 1.5332 | 63.3 63.1 | 7.4 7.6 | — — | 12.4 13.0 | — — | 11.3 10.6 | 4-Chloro-phenol |
| 28 | 4-(5-Isopropoxy-3-methyl-2-pentenyloxy)-anisole | $C_{16}H_{24}O_3$ | 264.4 | 1.5050 | 72.7 72.3 | 9.2 9.5 | — — | — — | — — | — — | 4-Methoxy-phenol |
| 29 | 4-(5-Isopropoxy-3-methyl-2-pentenyloxy)-thioanisole | $C_{16}H_{24}O_2S$ | 280.4 | 1.5329 | 68.5 68.0 | 8.6 8.6 | — — | — — | — — | 11.4 10.9 | 4-(Methyl-thio)-phenol |
| 30 | 4-(5-Isopropoxy-3-methyl-2-pentenyloxy)-ethylbenzol | $C_{17}H_{26}O_2$ | 262.4 | 1.4992 | 77.8 77.5 | 10.0 10.7 | — — | — — | — — | — — | 4-ethyl phenol |
| 31 | 4-(5-Isopropoxy-3-methyl-2-pentenyloxy)-nitrobenzol | $C_{15}H_{21}NO_4$ | 279.3 | 1.5335 | 64.5 64.4 | 7.6 7.7 | — — | — — | 5.0 4.8 | — — | 4-Nitro-phenol |
| 32 | 4-(5-Isopropoxy-3-methyl-2-pentenyloxy)-1,3-dichlorobenzol | $C_{15}H_{20}Cl_2O_2$ | 303.2 | 1.5244 | 59.4 59.4 | 6.6 6.6 | — — | 23.4 23.6 | — — | — — | 2,4-Dichloro-phenol |

EXAMPLE 33

5-(6-Ethoxy-3-methyl-2-hexenyloxy)-1,3-benzodioxol (according to process a)

2.21 g (0.01 mol) of 6-ethoxy-1-bromo-3-methyl-2-hexene are added at 5° and while stirring to 1.38 g (0.01 mol) of 3,4-methylendioxyphenol and 0.56 g (0.01 mol) of potassium hydroxide in 50 cc of 1,2-dimethoxyethane. After stirring at 5° for 2 hours the mixture is stirred at 20°–25° during the course of 60 hours, is subsequently filtered and the filtrate is evaporated at reduced pressure. The residue is taken up in ether, is washed with water, dried with sodium sulphate, and the ether is distilled off. After chromatography of the residue on silica gel with hexene/ethyl acetate 9:1, 5-(6-ethoxy-3-methyl-2-hexenyloxy)-1,3-benzodioxol is obtained as colourless oil. $n_D^{20} = 1.5192$.

| Analysis: | $C_{16}H_{22}O_4$ | Molecular weight: | 278.3 |
|---|---|---|---|
| Calc. | C 69.0 % | H 8.0 % | |
| Found | 68.9 % | 8.1 % | |

$n_D^{20} = 1.5266$

| Analysis: | $C_{17}H_{24}O_3$ | Molecular weight: | 276.4 |
|---|---|---|---|
| Calc. | C 73.9 % | H 8.8 % | |
| Found | 73.5 % | 8.8 % | |

EXAMPLE 36

5-(4-Isobutoxy-2-methyl-2-butenyloxy)-1,3-benzodioxol (according to process a)

2.21 g (0.01 mol) of 1-bromo-4-isobutoxy-2-methyl-2-butene are added at 0° during the course of 5 minutes to 1.38 g (0.01 mol) of 3,4-methylendioxy-phenol and 0.56 g (0.01 mol) of potassium hydroxide in 40 cc of 1,2-dimethoxyethane. After stirring the reaction mixture at room temperature for 24 hours it is filtered and the solvent is distilled off at reduced pressure. The residue is dissolved in ether, washed with saturated salt solution, dried with sodium sulphate and evaporated. The residue is purified by chromatography on silica gel with hexane/ethyl acetate 9:1. 5-(4-isopropoxy-2-methyl-2-butenyloxy)-1,3-benzodioxol is obtained as colourless oil. $n_D^{20} = 1.5150$.

| Analysis: | $C_{16}H_{22}O_4$ | | Molecular weight: | 278.3 |
|---|---|---|---|---|
| Calc. | C 69.0 % | H 8.0 % | | |
| Found | 69.0 % | 8.3 % | | |

EXAMPLE 37

5-(6-Isopropoxy-4-methyl-3-hexenyloxy)-1,3-benzodioxol (according to process a)

2.35 g (0.017 mol) of potassium carbonate and 50 mg of potassium iodide are added to a solution of 4.0 g (0.017 mol) of 1-bromo-6-isopropoxy-4-methyl-3-hexene and 2.35 g (0.017 mol) of 3,4-methylendioxyphenol in 120 cc of acetone. The suspension is boiled under reflux during the course of 20 hours, is then filtered and liberated from acetone in a vacuum. The residue is taken up in ether, washed with water and saturated salt solution, dried over sodium sulphate and evaporated. The residue is chromatographed on silica gel with hexane/ethyl acetate 9:1. Thus the cis/trans isomeric mixture of the 5-(6-isopropoxy-4-methyl methyl-3-hexenyloxy)-1,3-benzodioxol is obtained as colourless oil. $n_D^{20}$ = 1.5111.

| Analysis: | $C_{17}H_{24}O_4$ | | Molecular weight: | 292.4 |
|---|---|---|---|---|
| Calc. | C 69.8 % | H 8.3 % | O 21.9 % | |
| Found | 68.9 % | 8.5 % | 22.7 % | |

EXAMPLE 38

4'-(5-Isopropoxy-2-pentenyloxy)-acetophenone (according to process a)

3.4 g (0.06 mol) of pulverised potassium hydroxide are added to a solution of 8.2 g (0.06 mol) of p-hydroxy-acetophenone and 14.6 g (0.09 mol) of 1-chloro-5-isopropoxy-2-pentene in 100 cc of 1,2-dimethoxyethane. The mixture is stirred at 60° during the course of 24 hours and is subsequently filtered. The filtrate is evaporated at reduced pressure, the residue is taken up in ether, and the ether solution is washed with saturated salt solution. The organic phase is dried with sodium sulphate and evaporated. The residue is chromatographed with hexane/ethyl acetate 4:1 on silica gel and then the 4'-(5-isopropoxy-2-pentenyloxy)-acetophenone is obtained as colourless oil. $n_D^{20}$ = 1.5240.

| Analysis: | $C_{16}H_{22}O_3$ | | Molecular weight: | 262.3 |
|---|---|---|---|---|
| Calc. | C 73.3 % | H 8.5 % | O 18.3 % | |
| Found | 73.3 % | 8.6 % | 18.2 % | |

In analogous manner as described in Example 38, but using 3,4-methylendioxy-phenol in the place of p-hydroxy-acetophenone, the following compound of general formula I is produced:

EXAMPLE 39

5-(5-Isopropoxy-2-pentenyloxy)-1,3-benzodioxol $n_D^{20}$ = 1.5157

| Analysis: | $C_{15}H_{20}O_4$ | | Molecular weight: | 264.3 |
|---|---|---|---|---|
| Calc. | C 68.2 % | H 7.6 % | O 24.2 % | |
| Found | 68.4 % | 8.0 % | 24.1 % | |

EXAMPLE 40

4-[(5-Isopropoxy-2-pentenylthio)-methyl]-chlorobenzol (according to process a)

8.1 g (0.05 mol) of 1-chloro-5-isopropoxy-2-pentene are added dropwise at 20°–25° during the course of 10 minutes and while stirring to a solution of 7.9 g (0.05 mol) of 4-chloro-benzylmercaptan and 5.6 g (0.05 mol) of potassium tert.butoxide in 150 cc of tert-.butanol. The solution which is rendered turbid during the addition is stirred at 60° during the course of 1 hour and is then cooled and filtered. The solvent is distilled off at reduced pressure, the residue is dissolved in ether and the ether solution is washed with saturated salt solution. The ether phase is dried with sodium sulphate and then the ether is distilled off and the residue is chromatographed on silica gel with chloroform. The 4-[(5-isopropoxy-2-pentenylthio)-methyl]-chlorobenzol is obtained as colourless oil having a B.P. of 110°–112°/5.10$^{-4}$mm. $n_D^{20}$ = 1.5391.

| Analysis: | $C_{15}H_{21}ClOS$ | | Molecular weight: | | 284.8 |
|---|---|---|---|---|---|
| Calc. | C 63.3 % | H 7.4 % | Cl 12.4 % | S | 11.3 % |
| Found | 63.2 % | 7.4 % | 12.7 % | | 11.5 % |

EXAMPLE 41

5-[(5-Isopropoxy-3-methyl-2-pentenyloxy)-methyl]-1,3-benzodioxol (according to process a)

15.8 g (0.1 mol) of 5-isopropoxy-3-methyl-1-penten-3-ol are added dropwise at 5° during the course of 15 minutes and while stirring to 40 cc of 48% hydrobromic acid. After 30 minutes at 0°–5° the mixture is extracted with ether, the ether extract is extracted with 10% soda solution and subsequently with saturated salt solution, is dried with sodium sulphate and evaporated.

The obtained 1-bromo-5-isopropoxy-3-methyl-2-pentene (19.0 g) is added to 17.4 g (0.1 mol) of sodium salt of 3,4-methylendioxy-benzyl alcohol in 150 cc of dimethylformamide and the mixture is stirred at 60° for 5 hours. The reaction mixture is poured on 300 cc of water and extracted with ether. The ether solution is washed with water, dried with sodium sulphate and evaporated. The residue is chromatographed on silica gel with hexane/ethyl acetate 9:1. A mixture of cis and trans-5-[(5-isopropoxy-3-methyl-2-pentenyloxy)-methyl]-1,3-benzodioxol is obtained as colourless oil. $n_D^{20}$ = 1.5088.

| Analysis: | $C_{17}H_{24}O_4$ | | Molecular weight: | 292.4 |
|---|---|---|---|---|
| Calc. | C 69.8 % | H 8.3 % | | |
| Found | 69.4 % | 8.2 % | | |

In analogous manner as described in Example 41, but using 5-ethoxy-3,5-dimethyl-1-hexen-3-ol in the place of 5-isopropoxy-3-methyl-1-penten-3-ol, the following compound of general formula I is produced.

EXAMPLE 42

5-[(5-Ethoxy-3,5-dimethyl-2-hexenyloxy)-methyl]-1,3-benzodioxol $n_D^{20}$ = 1.5038

| Analysis: | $C_{18}H_{26}O_4$ | | Molecular weight: | 306.4 |
|---|---|---|---|---|
| Calc. | C 70.6 % | H 8.6 % | | |
| Found | 70.6 % | 9.2 % | | |

EXAMPLE 43

5-[(5-Isopropoxy-3-methyl-2-pentenyloxy)-methyl]-1,3-benzodioxol (according to process a)

8.0 g (0.2 mol) of sodium hydroxide are added to a solution of 30.4 g (0.2 mol) of 3,4-methylendioxy-benzylalcohol in 300 cc of benzene. The mixture is heated while stirring vigorously and kept at reflux temperature whereby the water condensing in a refrigerator is separated by means of a water separator. After 24 hours 35.3 g (0.2 mol) of 1-chloro-5-isopropoxy-3-methyl-2-pentene are added dropwise during the course of 1 hour and the mixture is stirred under reflux for a further 16 hours.

The reaction mixture is cooled and then washed with saturated salt solution, the benzene solution is dried with sodium sulphate, is dried and evaporated. The residue is fractionated at $10^{-4}$mm whereby the cis/trans mixture of 5-[(5-isopropoxy-3-methyl-2-pentenyloxy)-methyl]-1,3-benzodioxol distils at 126°–136°.

The product is identical with the compound produced in accordance with Example 41.

EXAMPLE 44

5-(4-Isobutoxy-3-methyl-butenyloxy)--butanyloxy)-1,3-benzodioxol (according to process b)

1.6 g (0.0165 mol) of sodium-isobutylate in 75 cc of isobutanol are added dropwise at 70° during the course of 15 minutes to 4.3 g (0.015 mol) of 5-(4-bromo-3-methyl-2-butenyloxy)-1,3-benzodioxol which is dissolved in 130 cc of isobutanol After 3 hours at this temperature the reaction mixture is filtered, the solvent is distilled off at reduced pressure and the residue is dissolved in ether. The ether solution is washed with saturated salt solution, is dried with sodium sulphate and evaporated. The residue is chromatographed on silica gel with chloroform. 5-(4-isobutoxy-3-methyl-2-butenyloxy)-1,3-benzodioxol is obtained as colourless oil. $n_D^{20}$= 1.5158.

| Analysis: | $C_{16}H_{22}O_4$ | | Molecular weight: | 278.3 |
|---|---|---|---|---|
| Calc. | C 69.0 % | H 8.0 % | O 23.0 % | |
| Found | 68.3 % | 7.8 % | 23.5 % | |

In analogous manner as described in Example 44, but using n.butanol as solvent and sodium-n.butylate in the place of sodium-isobutylate, the following compound of general formula I is produced:

EXAMPLE 45

5-(4-n.Butoxy-3-methyl-2-butenyloxy)-1,3-benzodioxol $n_D^{20}$= 1.5168

| Analysis: | $C_{16}H_{22}O_4$ | | Molecular weight: | 278.3 |
|---|---|---|---|---|
| Calc. | C 69.0 % | H 8.0 % | O 23.0 % | |
| Found | 68.6 % | 8.2 % | 22.8 % | |

In analogous manner as described in Example 44, but using 4'-(4-bromo-3-methyl-2-butenyloxy)-acetophenone in the place of 5-(4-bromo-3-methyl-2-butenyloxy)-1,3-benzodioxol, the following compound of general formula I is produced:

EXAMPLE 46

4'-(4-Isobutoxy-3-methyl-2-butenyloxy)-acetophenone $n_D^{20}$= 1.5282

| Analysis: | $C_{17}H_{24}O_3$ | | Molecular weight: | 276.4 |
|---|---|---|---|---|
| Calc. | C 73.8 % | H 8.7 % | O 17.3 % | |
| Found | 73.4 % | 9.1 % | 18.1 % | |

In analogous manner as described in Example 46, but using the sodium salt of the allyl alcohol and allyl alcohol as solvent, the following compound of general formula I is produced.

EXAMPLE 47

4'-(4-Allyloxy-3-methyl-2-butenyloxy)-acetophenone $n_D^{20}$ = 1.5448

| Analysis: | $C_{16}H_{20}O_3$ | | Molecular weight: | 260.3 |
|---|---|---|---|---|
| Calc. | C 73.8 % | H 7.7 % | O 18.4 % |
| Found | 73.2 % | 7.8 % | 19.14 % |

In analogous manner as described in Example 44, but using 5-[(4-bromo-3-methyl-2-butenyloxy)-methyl]-1,3-benzodioxol in the place of 5-(4-bromo-3-methyl-2-butenyloxy)-1,3-benzodioxol, the following compound of general formula I is produced.

EXAMPLE 48

5-[(4-Isobutoxy-3-methyl-2-butenyloxy)-methyl]-1,3-benzodioxol $n_D^{20}$ = 1.5102

| Analysis: | $C_{17}H_{24}O_4$ | | Molecular weight: | 292.4 |
|---|---|---|---|---|
| Calc. | C 69.8 % | H 8.3 % | | |
| Found | 69.4 % | 8.1 % | | |

EXAMPLE 49

4'-(4-Benzylthio-3-methyl-2-butenyloxy)-acetophenone (according to process b)

14.15 g (0.05 mol) of 4'-(4-bromo-3-methyl-2-butenyloxy)- acetophenone are added at 10°–15° during the course of 1 hour to 7.3 g (0.05 mol) of sodium salt of benzylmercaptan which is dissolved in 120 cc of dimethylformamide. The mixture is stirred at 20°–25° for 20 hours, is subsequently filtered and the filtrate is evaporated at reduced pressure. The residue is dissolved in ether, is extracted with saturated salt solution and the ether solution is evaporated. The remaining yellowish oil is chromatographed on silica gel with hexane/ethyl acetate 2:1. After recrystallization from ether/hexane the 4'-(4-benzylthio-3-methyl-2-butenyloxy)-acetophenone is obtained as colourless crystals. M.P. 75°–76.5°.

| Analysis: | $C_{20}H_{22}O_2S$ | | Molecular weight: | | 326.5 |
|---|---|---|---|---|---|
| Calc. | C 73.6 % | H 6.8 % | | S | 9.8 % |
| Found | 73.3 % | 6.7 % | | | 9.7 % |

EXAMPLE 50

5-(4-Isobutylthio-3-methyl-2-butenyloxy)-1,3-benzodioxol (according to process b)

A solution of 4.3 g (0.015 mol) of 5-(4-bromo-3-methyl-2-butenyloxy)-1,3-benzodioxol in 50 cc of benzene is added at 25° to 1.7 g (0.015 mol) of sodium-isobutylthio alcoholate in 30 cc of benzene. The mixture is kept at reflux temperature for 13 hours, is subsequently filtered, washed with saturated salt solution and evaporated. The remaining yellow oil is chromatographed with hexane/ethyl acetate 7:1 on silica gel, whereby colourless 5-(4-isobutylthio-3-methyl-2-butenyloxy)-1,3-benzodioxol is obtained. $n_D^{20}$ = 1.5463.

| Analysis: | $C_{16}H_{22}O_3S$ | | Molecular weight: | | 294.4 |
|---|---|---|---|---|---|
| Calc. | C 65.3 % | H 7.5 % | | S | 10.9 % |
| Found | 65.1 % | 7.6 % | | | 10.6 % |

In analogous manner as described in Example 50 the following compound of general formula I is produced, whereby in the place of 5-(4-bromo-3-methyl-2-butenyloxy)-1,3-benzodioxol 4-(4-bromo-3-methyl-2-butenyloxy)-benzoic methyl ester is used.

EXAMPLE 51

4-(4-Isobutylthio-3-methyl-2-butenyloxy)-benzoic methyl ester $n_D^{20}$ = 1.5428

| Analysis: | $C_{17}H_{24}O_3S$ | | Molecular weight: | | 308.4 |
|---|---|---|---|---|---|
| Calc. | C 66.2 % | H 7.8 % | | S | 10.4 % |
| Found | 65.2 % | 7.8 % | | | 9.8 % |

EXAMPLE 52

4-(4-Isobutoxy-3-methyl-2-butenyloxy)-benzoic methyl ester (according to process b)

A solution of 6.0 g (0.02 mol) of 4-(4-bromo-3-methyl-2-butenyloxy)-benzoic methyl ester and 2.9 g (0.03 mol) of sodium-isobutylate in 130 g of isobutanol is stirred at 70° for 6 hours. After this period the reaction mixture is filtered, the filtrate is evaporated at reduced pressure. The residue is dissolved in ether, the ether solution is washed with saturated salt solution, dried with sodium sulphate and evaporated. The residue (6.5 g) is dissolved in 50 cc of absolute methanol, 0.54 g (0.01) mol of sodium methylate is added and the mixture is boiled under reflux for 2 hours. After this period 40 cc of methanol are distilled off. The remaining residue is dissolved in 100 cc of ether, the ether solution is extracted twice with 100 cc amounts of saturated salt solution and dried with sodium sulphate. The ether is distilled off and the resulting 4-(4-isobutoxy-3-methyl-2-butenyloxy)-benzoic methyl ester is purified by chromatography on silica gel with hexane/ethyl acetate 20:1. $n_D^{20}$ = 1.5151.

| Analysis: | $C_{17}H_{24}O_4$ | | Molecular weight: | | 292.4 |
|---|---|---|---|---|---|
| Calc. | C 69.8 % | H 8.3 % | O | | 21.9 % |
| Found | 70.0 % | 8.4 % | | | 22.1 % |

EXAMPLE 53

5-(4-Isobutoxy-2-butenyloxy)-1,3-benzodioxol (according to process b)

1.9 g (0.02 mol) of sodium-isobutylate in 30 cc of isobutanol are added dropwise at 50° during the course of 2hours to a solution of 5.4 g (0.02 mol) of 5-(4-bromo-2-butenyloxy)-1,3-benzodioxol in 100 cc of isobutanol. After stirring the reaction mixture at 50° for 6 hours it is filtered and the solvent of the filtrate is distilled off at reduced pressure. The remaining oil is dissolved in either, the ether solution is extracted with water, dried with sodium sulphate and evaporated. The residue is chromatographed with hexane/ethyl acetate 12:1 on silica gel, whereby the 5-(4-isobutoxy-2-butenyloxy)-1,3-benzodioxol is obtained as colourless oil. $n_D^{20}$ = 1.5102.

| Analysis: | $C_{15}H_{20}O_4$ | Molecular weight: | 264.3 |
|---|---|---|---|
| Calc. | C 68.2 % | H 7.6 % | |
| Found | 67.4 % | 7.5 % | |

The following compound is produced in manner analogous to that described in Example 53, but using 4'-(4-bromo-2-butenyloxy)-acetophenone in the place of 5-(4-bromo-2-butenyloxy)-1,3-benzodioxol.

EXAMPLE 54

4'-(4-Isobutoxy-2-butenyloxy)-acetophenone $n_D^{20}$ = 1.5262

| Analysis: | $C_{16}H_{22}O_3$ | Molecular weight: | 262.3 |
|---|---|---|---|
| Calc. | C 73.3 % | H 8.5 % | |
| Found | 73.5 % | 8.6 % | |

In manner analogous to that described in Example 53 the following compound is produced, whereby 5-[(4-bromo-2-butenyloxy)-methyl]-1,3-benzodioxol is used in the place of 5-(4-bromo-2-butenyloxy)-1,3-benzodioxol:

EXAMPLE 55

5-[(4-Isobutoxy-2-butenyloxy)-methyl]-1,3-benzodioxol $n_D^{20}$ = 1.5110

| Analysis: | $C_{16}H_{22}O_4$ | Molecular weight: | 278.3 |
|---|---|---|---|
| Calc. | C 69.0 % | H 8.0 % | |
| Found | 68.7 % | 7.9 % | |

EXAMPLE 56

5-(7-Isopropoxy-5-methyl-4-heptenyloxy)-1,3-benzodioxol (according to process c)

A mixture of 2.5 g (0.013 mol) of 7-isopropoxy-5-methyl-4-cis,trans-heptenol, 1.25 g (0.009 mol) of 3,4-methylendioxy-phenol, and 2.22 g (0.011 mol) of dicyclohexyl carbodiimide are stirred at 100° for 18 hours. After cooling the residue is chromatographed with hexane/ethyl acetate 99:1 on silica gel. A cis,trans mixture of 5-(7-isopropoxy-5-methyl-4-heptenyloxy)-1,3-benzodioxol is obtained. $n_D^{20} = 1.5017$.

| Analysis: | $C_{18}H_{26}O_4$ | Molecular weight: | 306.4 |
|---|---|---|---|
| Calc. | C 70.6 % | H 8.6 % | |
| Found | 70.8 % | 8.8 % | |

EXAMPLE 57

5-(5-Isopropoxy-2-pentenyloxy)-1,3-benzodioxol (according to process c)

A mixture of 7.2 g (0.05 mol) of 5-isopropoxy-2-penten-1-ol, 6.9 g (0.05 mol) of 3,4-methylendioxy-phenol, and 10.3 g (0.05 mol) of dicyclohexyl-carbodiimide is stirred at 105° for 16 hours. After cooling 50 cc of ether are added, the mixture is filtered and the filtrate is evaporated. The residue is chromatographed on silica gel with hexane/ethyl acetate 9:1 and 5-(5-isopropoxy-2-pentenyloxy)-1,3-benzodioxol is obtained as colourless oil which is identical with the product produced in accordance with Example 39.

EXAMPLE 58

4-[(5-Isopropoxy-2-pentenylthio)-methyl]-chlorobenzol (according to process d)

A solution of 8.0 g (0.05 mol) of 5-isopropoxy-2-penten-1-thiol and 2 g (0.05 mol) of sodium hydroxide in 30 cc of ethanol are added dropwise at 50° during the course of 45 minutes to a solution of 8.05 g (0.05 mol) of p-chloro-benzylchloride in 25 cc of ethanol, the temperature not exceeding 55°. After the addition is complete the mixture is heated to 60° during 10 minutes. The reaction mixture is filtered, the ethanol is distilled off and the residue is chromatographed on silica gel with chloroform, whereby 4-[(5-isopropoxy-2-pentenylthio)-methyl]-chlorobenzol is obtained which is identical with the compound produced in accordance with Example 40.

EXAMPLE 59

5-[(5-Isopropoxy-3-methyl-2-pentenyloxy)-methyl]-1,3-benzodioxol (according to process d)

3.16 g (0.02 mol) of 5-isopropoxy-3-methyl-2-penten-1-ol are added at room temperature to a solution of 1.36 g (0.02 mol) of sodium ethylate in 30 cc of ethanol. The solvent is distilled off at reduced pressure and the residue which is dried well at room temperature is dissolved in 30 cc of dimethylsulphoxide. 4.3 g (0.02 mol) of 3,4-methylendioxy-benzylbromide (produced according to P. Karrer et al., Helv. chim. Acta 6, 905 [1923]) which are dissolved in 20 cc of dimethylsulphoxide are added dropwise at 0° to this solution. The mixture is stirred at room temperature for 2 hours and subsequently at 60° for 18 hours.

The reaction mixture is poured on 200 cc of water, is extracted with ether and the ether extract is washed with saturated salt solution. After the drying of the ether extract with sodium sulphate and distillation of the solvent the residue is chromatographed on silica gel with hexane/ethyl acetate 9:1. The resulting cis/trans isomeric mixture of 5-[(5-isopropoxy-3-methyl-2-pentenyloxy)-methyl]-1,3-benzodioxol is identical with the isomeric mixture produced in accordance with Example 41.

EXAMPLE 60

1,4-Bis(1,3-benzodioxol-5-yloxy)-2-methyl-2-butene 3.2 g (0.02 mol) of sodium salt of 3,4-methylendioxy-phenol are suspended in 60 cc of 1,2-dimethoxyethane and cooled to 0°–5°. 2.28 g (0.01 mol) of 1,4-dibromo-2-methyl-2-butene, dissolved in 20 cc of 1,2-dimethoxyethane are added while stirring. The mixture is stirred at 20°–25° during the course of 20 hours and at 50° during the course of 5 hours; it is subsequently filtered and the filtrate is evaporated. The residue is taken up in ether, extracted with saturated salt solution, the ether phase is dried with sodium sulphate and evaporated. The obtained viscous oil is purified by chromatography on silica gel with hexane/ethyl acetate 5:1 and subsequently by crystallization from ethyl acetate/hexane. M.P. 73.5°–74°.

| Analysis: | $C_{19}H_{18}O_6$ | Molecular weight: | 342.3 |
|---|---|---|---|
| Calc. | C 66.7 % | H 5.3 % | |
| Found | 66.7 % | 5.6 % | |

In analogous manner as described in Example 60, but using sodium salt of 4-hydroxy-benzoic methyl ester in the place of the sodium salt of 3,4-methylendioxy-phenol, the following compound is produced.

EXAMPLE 61

4,4'-(2-Methyl-2-buten-1,4-ylendioxy)-bis(benzoic methyl ester)

M.P. 134°–135°

| Analysis: | $C_{21}H_{22}O_6$ | Molecular weight: | 370.4 |
|---|---|---|---|
| Calc. | C 68.1 % | H 6.0 % | O 25.9 % |
| Found | 68.6 % | 6.2 % | 25.5 % |

In analogous manner as described in Example 60, but using the sodium salt of 3,4-methylendioxy-benzylalcohol in the place of the sodium salt of 3,4-methylendioxy-phenol, the following compound is produced.

EXAMPLE 62

1,4-Bis(piperonyloxy)-2-methyl-2-butene $n_D^{20} = 1.5537$

| Analysis: | $C_{21}H_{22}O_6$ | Molecular weight: | 370.4 |
|---|---|---|---|
| Calc. | C 68.1 % | H 6.0 % | |
| Found | 68.0 % | 6.5 % | |

The alcohols of general formula VIII required for the production of the compounds of formula I without isolation of the compounds of general formula II may be produced in accordance with the following Example:

EXAMPLE 63

5-Isopropoxy-3-methyl-1-penten-3-ol 12 g (0.5 mol) of magnesium cuttings are covered with a layer of 60 cc of absolute tetrahydrofurane in an atmosphere of nitrogen in a flask equipped with a stirrer and a reflux condenser cooled with ice, and are heated to 40°–45°. 5 cc of a solution of 53.5 g (0.5 mol) of vinyl bromide in 100 cc of absolute tetrahydrofurane are added dropwise by means of a dropping funnel, whereupon an exothermic reaction sets in. The remaining vinyl bromide solution is added dropwise at such a rate that the reaction mixture maintains a temperature of 45° to 50° (approximately 1 to 1½ hours). Then the mixture is stirred at 50° for 1 hour and subsequently cooled to 0°. 52 g (0.4 mol) of 4-isopropoxy-2-butanone in 100 cc of absolute tetrahydrofurane are added dropwise during the course of 45 minutes and while stirring vigorously; the reaction mixture is subsequently stirred at room temperature during the course of 16 hours. After this period 250 cc of a 20% ammonium chloride solution are added during the course of 15 minutes to the reaction mixture which is cooled to 5°–10°. The mixture is stirred for 15 minutes and extracted with ether. The ether extract is washed with water in a separatory funnel, is dried with sodium sulphate and evaporated. The residue is fractionated at 13 mm pressure, whereby the 5-isopropoxy-3-methyl-1-penten-3-ol distils at 72°–73°.$n_D^{20}$: 1.4297.

| Analysis: | $C_9H_{18}O_2$ | | Molecular weight: | 158.2 |
|---|---|---|---|---|
| Calc. | C | 68.3 % | H | 11.5 % |
| Found | | 68.1 % | | 11.4 % |

The compounds of general formula II may be produced in accordance with the following Example:

EXAMPLE 78

6-Ethoxy-1-bromo-3-methyl-2-hexene 3.9 g (0.03 mol) of 5-ethoxy-2-pentanone (produced in accordance with A. H. Tracy et al. J. Org. Chem. 6, 68 [1941]) in 10 cc of tetrahydrofurane are added dropwise at 0° during the course of 30 minutes and while stirring to the Grignard reagent, produced from 0.96 g (0.04 mol) of magnesium and 4.3 g (0.04 mol) of vinyl bromide in 20 cc of tetrahydrofurane. After stirring at 20°–25° for 15 hours the mixture is cooled to 5°–10°; 25 cc of 20% ammonium chloride solution are added and after 10 minutes it is extracted with ether. The ether extract is washed with saturated salt solution, dried with sodium sulphate and evaporated. The residue which is uniform in accordance with gas-chromatography (4.5 g of 6-ethoxy-3-methyl-1-hexen-3-ol) is added at 0° during the course of 5 minutes to 12 cc of 48% hydrobromic acid. The mixture is stirred at 0°–5° during the course of 30 minutes and then the ether is extracted, the ether solution is washed with saturated salt solution, dried with sodium sulphate and evaporated. The resulting 6-ethoxy-1-bromo-3-methyl-2-hexene is used without purification.

EXAMPLE 79

1-Bromo-4-isobutoxy-2-methyl-2-butene 6.8 g (0.03 mol) of 1,4-dibromo-2-methyl-2-butene are dissolved in 15 cc of isobutanol and 2.9 g (0.03 mol) of sodium isobutylate in 50 cc of isobutanol are added at 0°. After stirring at 0° for 2 hours the mixture is stirred at 20°–25° for 16 hours. The mixture is filtered and the filtrate is evaporated at reduced pressure. The residue is dissolved in ether, washed with saturated salt solution and dried with sodium sulphate. The ether is evaporated and the residue is distilled at 13 mm. The product has a B.P. of 128°–138°/13 mm.

| Example | | Empirical formula | Molecular weight | B.P./mm | $n_D^{20}$ | Analysis % Calc. Found | | | Starting compound of formula IX |
|---|---|---|---|---|---|---|---|---|---|
| | | | | | | C | H | S | |
| 64 | 3-ethyl-5-isopropoxy-1-penten-3-ol | $C_{10}H_{20}O_2$ | 172.3 | 81–84°/12 | 1.4346 | 69.7 | 11.7 | — | 1-Isopropoxy-3-pentanone |
| | | | | | | 69.4 | 11.5 | — | |
| 65 | 5-sec.Butoxy-3-methyl-1-penten-3-ol | $C_{10}H_{20}O_2$ | 172.3 | 87–91°/15 | 1.4352 | 69.7 | 11.7 | — | 4-sec.Butoxy-2-butanone |
| | | | | | | 69.6 | 11.6 | — | |
| 66 | 3-ethyl-5-sec.butoxy-1-penten-3-ol | $C_{11}H_{22}O_2$ | 186.3 | 113–15°/30 | 1.4380 | 70.9 | 11.9 | — | 1-sec.Butoxy-3-pentanone |
| | | | | | | 71.2 | 11.8 | — | |
| 67 | 5-tert.Butoxy-3-methyl-1-penten-3-ol | $C_{10}H_{20}O_2$ | 172.3 | 78–81°/12 | 1.4316 | 69.7 | 11.7 | — | 4-tert.Butoxy-2-butanone |
| | | | | | | 69.2 | 11.4 | — | |
| 68 | 5-Isopropylthio-3-methyl-1-penten-3-ol | $C_9H_{18}OS$ | 174.3 | 79–80°/1.2 | 1.4813 | 62.0 | 10.4 | 18.4 | 4-Isopropylthio-2-butanone |
| | | | | | | 61.5 | 10.4 | 18.9 | |
| 69 | 5-sec.Butylthio-3-methyl-1-penten-3-ol | $C_{10}H_{20}OS$ | 188.3 | 86–89°/0.85 | 1.4844 | 63.8 | 10.7 | 17.0 | 4-sec.Butylthio-2-butanone |
| | | | | | | 63.3 | 10.5 | 17.4 | |
| 70 | 5-Cyclohexyloxy-3-methyl-1-penten-3-ol | $C_{12}H_{22}O_2$ | 198.3 | 87–90°/0.6 | 1.4669 | 72.7 | 11.2 | — | 4-Cyclohexyloxy-2-butanone |
| | | | | | | 72.8 | 11.6 | — | |
| 71 | 5-Cyclopentyloxy-3-methyl-1-penten-3-ol | $C_{11}H_{20}O_2$ | 184.3 | 76–79°/1.2 | 1.4612 | 71.7 | 10.9 | — | 4-Cyclopentyloxy-2-butanone |
| | | | | | | 71.6 | 11.0 | — | |
| 72 | 3-Methyl-5-(2-pentyloxy)-1-penten-3-ol | $C_{11}H_{22}O_2$ | 186.3 | 64–67°/1.0 | 1.4358 | 70.9 | 11.9 | — | 4-(2-Pentyloxy)-2-butanone |
| | | | | | | 70.4 | 12.2 | — | |
| 73 | 3-Methyl-5-(3-pentyloxy)-1-penten-3-ol | $C_{11}H_{22}O_2$ | 186.3 | 66–69°/1.0 | 1.4377 | 70.9 | 11.9 | — | 4-(3-Pentyloxy)-2-butanone |
| | | | | | | 70.3 | 11.8 | — | |
| 74 | 5-n.Butoxy-3-methyl-1-penten-3-ol | $C_{10}H_{20}O_2$ | 172.3 | 115–19°/33 | 1.4370 | 69.7 | 11.7 | — | 4-n.Butoxy-2-butanone |
| | | | | | | 69.3 | 11.5 | — | |
| 75 | 5-ethoxy-3-methyl-1-penten-3-ol | $C_8H_{16}O_2$ | 144.2 | 90–92°/46 | 1.4325 | 66.6 | 11.2 | — | 4-ethoxy-2-butanone |
| | | | | | | 66.9 | 11.0 | ... | |
| 76 | 5-ethoxy-3,5-dimethyl-1-hexen-3-ol | $C_{10}H_{20}O_2$ | 172.3 | 87–89°/16 | 1.4383 | 69.7 | 11.7 | — | 4-ethoxy-4-methyl-2-pentanone*) |
| | | | | | | 69.3 | 11.6 | — | |
| 77 | 3-Methyl-5-(6-Methyl-5-hepten-2-yloxy)-1-penten-3-ol | $C_{14}H_{26}O_2$ | 226.4 | | 1.4627 | 74.3 | 11.6 | — | 4-(6-Methyl-5-hepten-2-yloxy)-2-butanone |
| | | | | | | 74.0 | 11.5 | — | |

*)produced in accordance with A. Hoffman, J. Amer. chem. Soc. 49, 532 [1927]

| Analysis: | $C_9H_{17}BrO$ | | Molecular weight: | 221.1 |
|---|---|---|---|---|
| Calc. | C 48.9 % | H 7.7 % | Br 36.1 % | |
| Found | 49.0 % | 7.8 % | 35.6 % | |

The compounds of general formula II via formula XIV may be produced in accordance with the following Example:

EXAMPLE 80

1-Bromo-6-isopropoxy-4-methyl-3-hexene

A solution of 46 g (0.35 mol) of 4-isopropoxy-2-butanene in 100 cc of absolute tetrahydrofurane is added dropwise at 5° during the course of 10 minutes in an atmosphere of nitrogen and while stirring to the Grignard reagent (according to E. Renk et al., J. Amer. Chem. Soc. 83, 1987 [1961]) produced from 9.06 g (0.38 mol) of magnesium and 42.8 g (0.35 mol) of cyclopropyl bromide in 460 cc of absolute tetrahydrofurane. After stirring the reaction mixture at room temperature for 20 hours saturated ammonium chloride solution and ice are added and the mixture is extracted with ether. The ether extract is washed with saturated salt solution, dried over sodium sulphate and evaporated. The resulting 2-cyclopropyl-4-isopropoxy-2-butanol, having a B.P. of 75°–77°/12 mm, may be worked up without purification.

19 cc of 48% hydrobromic acid are added dropwise at 0° during the course of 15 minutes and while stirring to 27.7 g of crude product. The mixture is stirred at 0°–5° during the course of 30 minutes and subsequently extracted with ether. The ether extract is washed with water, saturated sodium bicarbonate, and saturated salt solution, dried over sodium sulphate and evaporated. The residue (20.2 g) is chromatographed with hexane/ethyl acetate 98:2 and 95:5 on 1 kg of silica gel. A chromatographically uniform cis/trans isomeric mixture of 1-bromo-6-isopropoxy-4-methyl-3-hexene is thus obtained. $n_D^{20} = 1.4721$

| Analysis: | $C_{10}H_{19}BrO$ | | Molecular weight: | 235.2 | |
|---|---|---|---|---|---|
| Calc. | C 51.1 % | H 8.1 % | Br 34.0 % | O 6.8 % | |
| Found | 50.8 % | 8.0 % | 34.2 % | 7.0 % | |

The compounds of formula IX required for the production of the compounds of formulae VIII and XIV may, for example, be produced in accordance with the following Example:

EXAMPLE 81

4-Isopropoxy-2-butanone 0.3 g of concentrated sulphuric acid are added to 7.2 g (0.12 mol) of isopropanol. A mixture of 21 g (0.3 mol) of vinyl methyl ketone and 36 g (0.6 mol) of isopropanol is added dropwise at room temperature during the course of 1 hour and while stirring, the temperature not exceeding 30°. After 24 hours 1.6 g of potassium carbonate and 2 drops of water are added at room temperature, the mixture is stirred vigorously for 2 hours and filtered; the clear filtrate which now reacts neutrally is fractionated at 36 mm. The excess of isopropanol distils and then the 4-isopropoxy-2-butanone at 73°–76°/136 mm.

| Analysis: | $C_7H_{14}O_2$ | Molecular weight: | 130.2 |
|---|---|---|---|
| Calc. | C 64.6 % | H 10.8 % | |
| Found | 64.1 % | 10.8 % | |

In analogous manner as described in Example 81, but using 6-methyl-5-hepten-2-ol in the place of isopropanol, the following compound is used.

EXAMPLE 82

4-(6-Methyl-5-hepten-2-yloxy)-2-butanone

B.P. 82–85°/1.0 mm    $n_D^{20} = 1.4462$
Analysis: $C_{12}H_{22}O_2$    Molecular weight: 198.3

| Calc. | C 72.7 % | H 11.2 % |
|---|---|---|
| Found | 71.8 % | 11.1 % |

The compounds of general formula II, wherein Y signifies oxygen and Hal signifies chlorine, may, for example, be produced as follows:

EXAMPLE 83

1-Chloro-5-isopropoxy-3-methyl-2-pentene 32.4 g of chloromethyl-isopropylether are added dropwise at 0° during the course of 40 minutes and while stirring to 20.4 g (0.3 mol) of isoprene and 0.3 g of zinc chloride. The mixture is then stirred at room temperature for 24 hours. The reaction mixture is taken up in ether, is washed with water and subsequently with sodium bicarbonate solution and again with water. The ether phase is dried with sodium sulphate, the ether is distilled off and the residue is distilled at 12 mm, whereby 1-chloro-5-isopropoxy-3-methyl-2-pentene is obtained as colourless oil. B.P. 86°–92°/12 mm, $n_D^{20} = 1.4553$.

| Analysis: | $C_9H_{17}ClO$ | | Molecular weight: | 176.7 |
|---|---|---|---|---|
| Calc. | C 61.2 % | H 9.7 % | Cl 20.1 % | |
| Found | 61.3 % | 9.6 % | 20.3 % | |

EXAMPLE 84

1-Chloro-5-isopropoxy-2-pentene 13 g (0.24 mol) of butadiene are introduced at 10°–15° during the course of 1½ hours and while stirring into a suspension of 0.8 g of newly melted zinc chloride in 21.7 g (0.2 mol) of chloromethyl-isopropylether. The mixture which has now turned yellow is stirred at 10° for 1 hour. After this period 20 cc of 10% sodium carbonate solution are added dropwise, 100 cc of benzene are added and the aqueous phase is separated in a separatory funnel. The benzene solution is washed with 10% sodium carbonate solution and subsequently with water, is dried with magnesium sulphate and evaporated at reduced pressure. The residue is distilled at 90 mm. B.P. of 1-chloro-5-isopropoxy-2-pentene: 110°–112°/90 mm. $n_D^{20} = 1.4408$.

| Analysis: | $C_8H_{15}ClO$ | | Molecular weight: | 162.7 |
|---|---|---|---|---|
| Calc. | C 59.1 % | H 9.3 % | Cl 21.8 % | |

-continued

| Analysis: | $C_xH_{15}ClO$ | Molecular weight: | 162.7 |
|---|---|---|---|
| Found | 59.2 % | 9.3 % | 21.1 % |

The compounds of general formula IV may be produced in accordance with the following Example:

EXAMPLE 85

5-(4-Bromo-3-methyl-2-butenyloxy)-1,3-benzodioxol 25.1 g (0.11 mol) of 1,4-dibromo-2-methyl-2-butene are dissolved in 120 cc of 1,2-dimethoxyethane and cooled to −20°. 16.0 g (0.1 mol) of sodium salt of the 3,4-methylendioxy-phenol in 170 cc of 1,2-dimethoxyethane are added during the course of 15 minutes to this solution. After stirring at 0° for 1 hour and at 20° for 15 minutes the solvent is distilled off in a vacuum. The residue is disolved in ether, is washed with saturated salt solution and dried with sodium suplhate. The ether is evaporated and an oily residue remains which is purified by chromatography on silica gel with hexane/ethyl acetate 9:1.

| Analysis: | $C_{12}H_{13}BrO_3$ | | Molecular weight: | | 285.1 | |
|---|---|---|---|---|---|---|
| Calc. | C 50.5 % | H 4.6 % | | Br 28.0 % | O | 16.8 % |
| Found | 50.4 % | 4.5 % | | 28.3 % | | 17.0 % |

In analogous manner as described in Example 85, but using the sodium salt of p-hydroxy-acetophenone in the place of the sodium salt of 3,4-methylendioxy-phenol, the following compound of general formula IV is produced:

EXAMPLE 86

4'-(4-Bromo-3methyl-2-butenyloxyl)-acetophenone

| Analysis: | $C_{13}H_{15}BrO_2$ | | Molecular weight: | 283.2 |
|---|---|---|---|---|
| Calc. | C 55.1 % | H 5.3 % | Br | 28.2 % |
| Found | 54.7 % | 5.3 % | | 28.5 % |

In analogous manner as described in Example 85, but using the sodium salt of the 4-hydroxy-benzoic methyl ester in the place of the sodium salt of 3,4-methylendioxy-phenol, the following compound is produced.

EXAMPLE 87

4-(4-Bromo-3-methyl-2-butenyloxy)-benzoic methyl ester

M.P. 50°-52°

| Analysis: | $C_{13}H_{15}BrO_3$ | | Molecular weight: | 299.2 |
|---|---|---|---|---|
| Calc. | C 52.2 % | H 5.1 % | Br | 26.7 % |
| Found | 52.3 % | 5.1 % | | 26.4 % |

EXAMPLE 88

5-[(4-Bromo-3-methyl-2-butenyloxy)-methyl]-1,3-benzodioxol 8.7 g (0.05 mol) of sodium salt of the 3,4-methylendioxybenzylalcohol are added at 0° during the course of 15 minutes and while stirring to 12.5 g (0.055 mol) of 1,4-dibromo-2-methyl-2-butene which is dissolved in 100 cc of 1,2-dimethoxyethane. The mixture is stirred at 20°-25° for 16 hours and at 50° for 15 minutes. The solvent is then distilled off at reduced pressure and 100 cc amounts of water and ether are added to the residue. The aqueous phase is separated in a separatory funnel, the ether phase is extracted with saturated salt solution, is dried with sodium sulphate and evaporated. The residue is chromatographed on silica gel with hexane/ethyl acetate 9:1, whereby the 5-[(4-bromo-3-methyl-2-butenyloxy)-methyl]-1,3-benzodioxol is obtained as uniform colourless oil.

| Analysis: | $C_{13}H_{15}BrO_3$ | | Molecular weight: | 299.2 |
|---|---|---|---|---|
| Calc. | C 52.2 % | H 5.1 % | Br | 26.7 % |
| Found | 51.8 % | 5.0 % | | 27.6 % |

EXAMPLE 89

5-(4-Bromo-2-butenyloxy)-1,3-benzodioxol 6.4 g (0.04 mol) of sodium salt of 3,4-methylendioxyphenol are added at −20° to a solution of 8.6 g (0.04 mol) of 1,4-dibromo-2-butene in 100 cc of 1,2-dimethoxyethane. The mixture is stirred at 0° for 3 hours and subsequently at room temperature for 1 hour. The solvent is distilled off at reduced pressure and the residue is taken up in ether. The ether solution is extracted with saturated salt solution, is dried with sodium sulphate and evaporated. The residue is purified by chromatography on silica gel with hexane/ethyl acetate 9:1. The 5-(4-bromo-2-butenyloxy)-1,3-benzodioxol is obtained as colourless oil.

| Analysis: | $C_{11}H_{11}BrO_3$ | | Molecular weight: | 271.1 |
|---|---|---|---|---|
| Calc. | C 48.7 % | H 4.1 % | Br | 29.5 % |
| Found | 48.6 % | 4.2 % | | 29.9 % |

In analogous manner as described in Example 89, but using the sodium salt of p-hydroxy-acetophenone in the place of the sodium salt of 3,4-methylendioxy-phenol, the following compound is produced:

EXAMPLE 90

4'-(4-Bromo-2-butenyloxy)-acetophenone

| Analysis: | $C_{12}H_{13}BrO_2$ | | Molecular weight: | 269.1 |
|---|---|---|---|---|
| Calc. | C 53.6 % | H 4.9 % | Br | 29.7 % |
| Found | 53.9 % | 5.1 % | | 30.7 % |

EXAMPLE 91

5-[(4-Bromo-2-butenyloxy)-methyl]-1,3-benzodioxol 11.8 g (0.055 mol) of 1,4-dibromo-2-butene and 8.7 g (0.05 mol) of sodium salt of 3,4-methylendioxy-benzylalcohol are covered with a layer of 100 cc of 1,2-dimethoxyethane. The mixture is stirred at 20°-25° for 16 hours and at 50° for 15 minutes. The solvent is subsequently distilled off at reduced pressure, the residue is taken up in ether and the ether solution is extracted with water. The organic phase is dried with sodium sulphate and the ether is then distilled off and the residue is chromatographed on silica gel with hexane/ethyl acetate 9:1. The chromatographically uniform 5-[(4-bromo-2-butenyloxy)-methyl-1,3-benzodioxol is obtained as slightly yellow oil.

| Analysis: | $C_{12}H_{13}BrO_3$ | Molecular weight: | 285.1 |
|---|---|---|---|
| Calc. | C 50.5 % | H 4.6 % | Br 28.0 % |
| Found | 50.4 % | 4.7 % | 27.5 % |

The compounds of general formula VI may be produced in accordance with the following Example:

EXAMPLE 92

7-Isopropoxy-5-methyl-4-heptenol

A solution of 3.68 g (0.02 mol) of 7-isopropoxy-5-methyl-4-cis, trans-heptenal in 6.5 cc of ethanol is added dropwise at 0°–5° during the course of 10 minutes and while stirring to a mixture of 0.76 g (0.02 mol) of sodium borohydride, 40 cc of water, 4 drops of 2N sodium hydroxide, and 40 cc of ethanol. After stirring for 2 hours at room temperature 60 cc of water are added to the reaction mixture which is concentrated by evaporation in a vacuum and extracted with ether after saturation with common salt. the ether extract is washed with water and saturated salt solution, dried over sodium sulphate and evaporated. The residue is chromatographed with hexane/ethyl acetate 9:1 on 180 g of silica gel, whereby pure 7-isopropoxy-5-methyl-4-cis,trans-heptenol is obtained.

| Analysis: | $C_{11}H_{22}O_2$ | Molecular weight: | 186.3 |
|---|---|---|---|
| Calc. | C 70.9 % | H 11.9 % | |
| Found | 70.9 % | 11.9 % | |

The compounds of general formula XVI are produced in accordance with the following Example:

EXAMPLE 93

7-Isopropoxy-5-methyl-4-heptenal 15.8 g (0.1 mol) of 5-isopropoxy-3-methyl-1-penten-3-ol: (produced in accordance with Example 63) and 20.0 g of mercury acetate are kept in 180 cc of ethylvinyl ether at reflux temperature during the course of 4 days. 0.9 cc of glacial acetic acid is added at 20° to the solution which has rendered turbid. 150 cc of 5% potassium carbonate solution are added after 3 hours and the mixture is extracted with hexane. The hexane extract is evaporated and the residue is heated to 165°–168° during 1½ hours in an atmosphere of nitrogen and without further purification; the residue is subsequently distilled at reduced pressure. B.P. of 7-isopropoxy-5-methyl-4-heptenal: 70°–73°/0.8 mm. $n_D^{20}$ = 1.4476

| Analysis: | $C_{11}H_{20}O_2$ | Molecular weight: | 184.3 |
|---|---|---|---|
| Calc. | C 71.7 % | H 10.9 % | |
| Found | 71.7 % | 10.8 % | |

EXAMPLE 94

5-Isopropoxy-2-penten-1-ol 8.13 g (0.05 mol) of 1-chloro-5-isopropoxy-2-pentene are added to a solution of 6.5 g of sodium carbonate in 60 cc of water and the mixture is heated to 95°–98° during 18 hours. After cooling the organic parts are extracted with benzene, the benzene extract is washed with saturated salt solution and dried with sodium sulphate. The solvent is distilled off and then it is distilled at reduced pressure. According to gas-chromatography pure 5-isopropoxy-2-penten-1-ol distils at 102°–104°/15 mm. $n_D^{20}$ = 1.4363.

| Analysis: | $C_8H_{16}O_2$ | Molecular weight: 144.2 | |
|---|---|---|---|
| Calc. | C 66.6 % | H 11.2 % | O 22.2 % |
| Found | 66.4 % | 11.0 % | 22.6 % |

In analogous manner as described in Example 94 the following compound is produced.

EXAMPLE 95

5-Isopropoxy-3-methyl-2-penten-1-ol

| $n_D^{20}$ = 1.4519 | | B.P. 115–118°/15 mm | |
|---|---|---|---|
| Analysis: | $C_9H_{18}O_2$ | Molecular weight: 158.2 | |
| Calc. | C 68.3 % | H 11.5 % | O 20.2 % |
| Found | 67.2 % | 11.3 % | 19.3 % |

EXAMPLE 96

5-Isopropoxy-2-penten-1-thiol

A mixture of 8.1 g (0.05 mol) of 1-chloro-5-isopropoxy-2-pentene, 3.8 g (0.05 mol) of thiourea, and 5 cc of water are heated to 98° during the course of 35 minutes and stirred at this temperature for 30 minutes. The homogeneous reaction mixture is cooled to 60° and 10 cc (0.05 mol) of 5N caustic soda solution are added dropwise at this temperature. The mixture which again has rendered heterogeneous is heated to 100° with stirring, is cooled after 5 minutes and poured on water The reaction mixture is extracted with ether, the ether extract is washed with saturated salt solution, is dried with sodium sulphate and the ether is evaporated. The residue is fractionated at 16 mm, whereby the 5-isopropoxy-2-penten-1-thiol is obtained as malodorous oil which is uniform according to gas-chromatography; it has a B.P. of 87°–89°/16 mm. $n_D^{20}$ = 1.4696.

| Analysis: | $C_8H_{16}SO$ | Molecular weight: 160.3 | | | |
|---|---|---|---|---|---|
| Calc. | C 60.0 % | H 10.1 % | S 20.0 % | O 10.0 % | |
| Found | 60.1 % | 10.1 % | 18.7 % | 10.9 % | |

EXAMPLE 97

5[4-Isobutoxy-2-methyl-2-butenyloxy)-methyl]-1,3-benzodioxol

In analogous manner to the process described in Example 43, the title compound is produced, employing the starting material 1-bromo-4-isobutoxy-2-methyl-2-butene (for production see Example 79) instead of 1-chloro-5-isopropoxy-3-methyl-2-pentene. $n_D^{20}$ = 1.5058

| Analysis: | $C_{17}H_{24}O_4$ | Molecular weight: 292.4 | |
|---|---|---|---|
| Calc. | C 60.8 % | H | 8.3 % |
| Found | 69.3 % | | 7.9 % |

EXAMPLE 98

4-(5-Isopropoxy-3-methyl-2-pentenyloxy)-tert.butylbenzene

In analogous manner to that described in Example 24, the title compound is produced, employing as starting material tert-butylphenol. $n_D^{20}$ = 1.4960

| Analysis: | $C_{19}H_{30}O_2$ | Molecular weight: 290.4 | |
|---|---|---|---|
| Calc. | C 78.6 % | H | 10.4 % |
| Found | 78.7 % | | 10.4 % |

EXAMPLE 99

4-(5-sec.Butoxy-3-methyl-2-pentenyloxy)-ethylbenzene

In analogous manner to the process described in Example 1, the title compound is produced, employing the starting material 5-sec.butoxy-3-methyl-1-pentene-3-ol (see Example 65) instead of 3-ethyl-5-sec.-butoxy-1-pentene-3-ol. $n_D^{20}$ = 1.4974

| Analysis: | $C_{18}H_{28}O_2$ | Molecular weight: 276.4 | |
|---|---|---|---|
| Calc. | C 78.2 % | H | 10.2 % |
| Found | 77.7 % | | 10.3 % |

EXAMPLE 100

4-[3-Methyl-5-(2-pentyloxy)-2-pentenyloxy]ethylbenzene

In analogous manner to the process described in Example 1, the title compound is produced, employing the starting material 3-methyl-5-(2-pentyloxy)-1-pentene-3-ol (see Example 72), instead of 3-ethyl-5-sec.-butoxy-1-pentene-3-ol. $n_D^{20}$ = 1.4973

| Analysis: | $C_{19}H_{30}O_2$ | Molecular weight: 290.4 | |
|---|---|---|---|
| Calc. | C 78.6 % | H | 10.4 % |
| Found | 78.4 % | | 10.5 % |

EXAMPLE 101

4-[3-Methyl-5-(3-pentyloxy)-2-pentenyloxyl]-ethylbenzene

In analogous manner to the process described in Example 1, the title compound is produced, employing the starting material 3-methyl-5-(3-pentyloxy)-1-pentene-3-ol (see Example 73), instead of 3-ethyl-5-sec.-butoxy-1-pentene-3-ol. $n_D^{20}$ = 1.4983

| Analysis: | $C_{19}H_{30}O_2$ | Molecular weight: 290.4 | |
|---|---|---|---|
| Calc. | C 78.6 % | H | 10.4 % |
| Found | 78.8 % | | 10.5 % |

EXAMPLE 102

4-](5-Isopropoxy-3-methyl-2-pentenyloxy)-methyl]-ethylbenzene

In analogous manner to the process described in Example 43, the title compound is produced, employing the starting material 4-ethylbenzylalcohol, instead of 3,4-methylenedioxybenzylalcohol. $n_D^{20}$ = 1.4972

| Analysis: | $C_{18}H_{28}O_2$ | Molecular weight: 276.4 | |
|---|---|---|---|
| Calc. | C 78.2 % | H | 10.2 % |
| Found | 77.5 % | | 10.0 % |

What is claimed is:

1. A method of combating insects in a locus comprising applying to the locus between 1 to 10 kilograms/hectare of a compound of the formula:

$$R_1-(CH_2)_s-Y-\underset{R_5}{\overset{R_4}{\underset{|}{C}}}\left(\underset{R_7}{\overset{R_6}{\underset{|}{C}}}\right)_v\left(\underset{R_9}{\overset{R_8}{\underset{|}{C}}}\right)_w-\underset{}{\overset{R_2}{C}}=\underset{}{\overset{R_3}{C}}-(CH_2)_z-X\underset{Z_q}{\underbrace{\bigcirc}}\underset{O}{\overset{O}{\diagdown}}(CR_{10}R_{11})_p$$

wherein
Z is alkyl of 1 to 5 carbon atoms, alkenyl of 2 to 12 carbon atoms, alkoxy of 1 to 5 carbon atoms, alkenyloxy of 2 to 12 carbon atoms, formyl, alkyl carbonyl of 2 to 6 carbon atoms, alkoxy carbonyl of 2 to 6 carbon atoms, mono- or di-alkyl substituted carbamoyl each alkyl substituent of which being of 1 to 5 carbon atoms, alkoxy methylene of 2 to 6 carbon atoms, alkylthio of 1 to 5 carbon atoms, fluoro, chloro, bromo, cyano or nitro,
$R_{10}$ and $R_{11}$ are independently hydrogen or alkyl of 1 to 5 carbon atoms,
$p$ is 1 or 2,
$q$ is 0 or 1,
$R_1$ is alkyl of 1 to 11 carbon atoms, an acylcic hydrocarbon of up to 11 carbon atoms having one or two double bonds or one triple bond, cycloalkyl of 4 to 7 carbon atoms, cycloalkyl of 4 to 7 carbon atoms substituted by alkyl of 1 to 5 carbon atoms, cycloalkenyl of 5 to 7 carbon atoms, cycloalkenyl of 5 to 7 carbon atoms substituted by alkyl of 1 to 5 carbon atoms, phenyl or

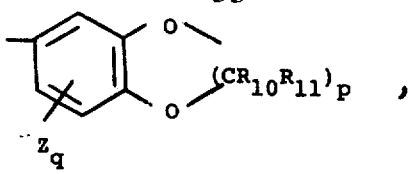

R hd 2, $R_3$, $R_4$, $R_5$, $R_6$, $R_7$, $R_8$ and $R_9$ are independently hydrogen, alkyl of 1 to 5 carbon atoms or alkenyl of 2 to 6 carbon atoms, Y is oxygen or sulfur, X is oxygen, sulfur, —OCH$_2$— or —SCH$_2$—, $s$, $v$ and $w$ are independently 0 or 1, and $z$ is 1, 2 or 3.

2. A method in accordance with claim 1 wherein the active ingredient is a compound of the formula:

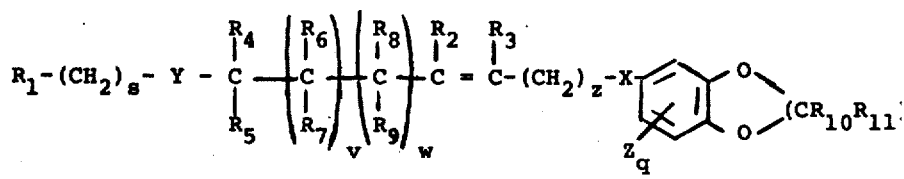

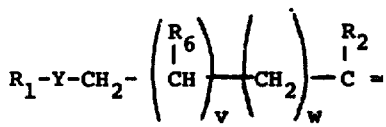

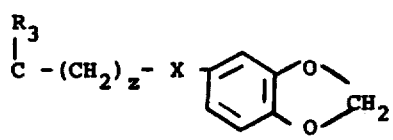

wherein $R_1$ is alkyl of 1 to 11 carbon atoms, alkenyl having up to 11 carbon atoms or cycloalkyl of 4 to 7 carbon atoms, Y is oxygen or sulfur, X is oxygen or -OCH$_2$-, $z$ is 1, 2 or 3, $v$ and $w$ are independently 0 or 1, and $R_2$, $R_3$ and $R_6$ are independently hydrogen or alkyl of 1 to 5 carbon atoms.

3. A method in accordance with claim 2 in which the compound is a compound in which $R_1$ is alkyl of 1 to 11 carbon atoms and $R_2$, $R_3$ and $R_6$ are independently hydrogen or methyl.

4. A method in accordance with claim 3 in which the compound is a compound in which $v$ is 0 and $R_1$ is branched alkyl of 3 to 5 carbon atoms.

5. A method in accordance with claim 3 in which the compound is a compound in which Y is oxygen.

6. A method in accordance with claim 4 in which the compound is a compound in which Y is oxygen, $R_3$ is hydrogen, X is oxygen, $R_2$ is methyl and $R_1$ is branched alkyl of 3 or 4 carbon atoms.

7. A method in accordance with claim 4 in which the compound is a compound in which Y is oxygen, $R_3$ is hydrogen, X is —OCH$_2$—, $R_2$ is methyl, $z$ is 1 and $R_1$ is branched alkyl of 3 or 4 carbon atoms.

8. The method of claim 1 in which the compound is 5-[(5-isopropoxy-3-methyl-2-pentenyloxy)-methyl]-1,3-benzodioxol.

9. The method of claim 1 in which the compound is 5-(5-isopropoxy-3-methyl-2-pentenyloxy)-1,3-benzodioxol.

10. The method of claim 1 in which the compound is 5-[(4-isobutoxy-3-methyl-2-butenyloxy)-methyl]-1,3-benzodioxol.

11. An insecticidal composition comprising an insecticide carrier or diluent and between 2 to 90% by weight of a compound of the formula:

wherein

Z is alkyl of 1 to 5 carbon atoms, alkenyl of 2 to 12 carbon atoms, alkoxy of 1 to 5 carbon atoms, alkenyloxy of 2 to 12 carbon atoms, formyl, alkyl carbonyl of 2 to 6 carbon atoms, alkoxy carbonyl of 2 to 6 carbon atoms, mono- or di-alkyl substituted carbamoyl each alkyl substituent of which being of 1 to 5 carbon atoms, alkoxy methylene of 2 to 6 carbon atoms, alkylthio of 1 to 5 carbon atoms, fluoro, chloro, bromo, cyano or nitro, $R_{10}$ and $R_{11}$ are independently hydrogen or alkyl of 1 to 5 carbon atoms, $p$ is 1 or 2, $q$ is 0 or 1, $R_1$ is alkyl of 1 to 11 carbon atoms, an acyclic hydrocarbon of up to 11 carbon atoms having one or two double bonds or one triple bond, cycloalkyl of 4 to 7 carbon atoms, cycloalkyl of 4 to 7 carbon atoms substituted by alkyl of 1 to 5 carbon atoms, cycloalkenyl of 5 to 7 carbon atoms, cycloalkenyl of 5 to 7 carbon atoms substituted by alkyl of 1 to 5 carbon atoms, phenyl or

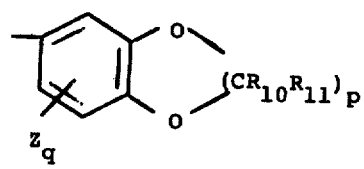

$R_2$, $R_3$, $R_4$, $R_5$, $R_6$, $R_7$, $R_8$ and $R_9$ are independently hydrogen, alkyl of 1 to 5 carbon atoms or alkenyl of 2 to 6 carbon atoms, Y is oxygen or sulfur, X is oxygen, sulfur, —OCH$_2$— or —SCH$_2$—, $s$, $v$ and $w$ are independently 0 or 1, and $z$ is 1, 2 or 3.

12. A composition in accordance with claim 11 in which the compound is a compound of the formula:

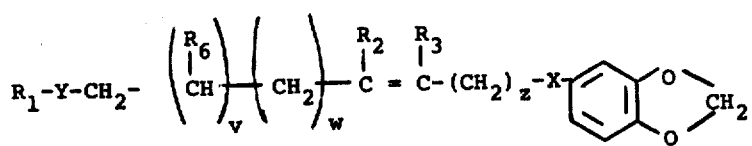
wherein
R₁ is alkyl of 1 to 11 carbon atoms, alkenyl having up to 11 carbon atoms or cycloalkyl of 4 to 7 carbon atoms,
Y is oxygen or sulfur,
X is oxygen or —OCH₂—,
z is 1, 2 or 3,
v and w are independently 0 or 1, and
R₂, R₃ and R₆ are independently hydrogen or alkyl of 1 to 5 carbon atoms.
* * * * *